(12) United States Patent
May et al.

(10) Patent No.: US 8,864,687 B2
(45) Date of Patent: Oct. 21, 2014

(54) METHOD AND APPARATUS FOR RESTORING ARTICULAR CARTILAGE

(76) Inventors: Thomas C. May, Wrentham, MA (US); Javin C. Pierce, Stowe, VT (US)

( * ) Notice: Subject to any disclaimer, the term of this patent is extended or adjusted under 35 U.S.C. 154(b) by 344 days.

(21) Appl. No.: 13/235,960

(22) Filed: Sep. 19, 2011

(65) Prior Publication Data

US 2012/0109335 A1 May 3, 2012

Related U.S. Application Data

(60) Provisional application No. 61/383,823, filed on Sep. 17, 2010.

(51) Int. Cl.
| | |
|---|---|
| A61B 5/103 | (2006.01) |
| A61B 5/117 | (2006.01) |
| A61F 2/46 | (2006.01) |
| A61B 5/107 | (2006.01) |
| A61B 10/02 | (2006.01) |
| A61F 2/30 | (2006.01) |
| A61B 19/00 | (2006.01) |

(52) U.S. Cl.
CPC ......... *A61B 19/46* (2013.01); *A61F 2002/3009* (2013.01); *A61B 2217/005* (2013.01); *A61F 2/4657* (2013.01); *A61F 2002/30599* (2013.01); *A61F 2002/4627* (2013.01); *A61F 2002/4658* (2013.01); *A61B 5/1076* (2013.01); *A61F 2/4684* (2013.01); *A61F 2002/4663* (2013.01); *A61F 2002/3096* (2013.01); *A61B 2019/461* (2013.01); *A61B 10/025* (2013.01); *A61F 2/30756* (2013.01); *A61F 2/4618* (2013.01)
USPC .......................................................... 600/587

(58) Field of Classification Search
USPC ...................... 600/564, 587, 594, 595; 606/99
See application file for complete search history.

(56) References Cited

U.S. PATENT DOCUMENTS

| | | | |
|---|---|---|---|
| 5,010,892 A | 4/1991 | Colvin et al. | |
| 5,824,055 A * | 10/1998 | Spiridigliozzi et al. | 623/1.11 |
| 6,159,179 A * | 12/2000 | Simonson | 604/117 |
| 6,406,476 B1 | 6/2002 | Kirwan, Jr. et al. | |
| 8,469,980 B2 * | 6/2013 | Sengun et al. | 606/167 |
| 2001/0011170 A1 | 8/2001 | Davison et al. | |
| 2002/0177859 A1 | 11/2002 | Monassevitch et al. | |
| 2004/0193154 A1 * | 9/2004 | Leatherbury et al. | 606/53 |
| 2004/0267277 A1 * | 12/2004 | Zannis et al. | 606/99 |
| 2007/0043376 A1 * | 2/2007 | Leatherbury et al. | 606/99 |
| 2008/0306408 A1 * | 12/2008 | Lo | 600/587 |
| 2009/0112119 A1 | 4/2009 | Kim | |

* cited by examiner

*Primary Examiner* — Adam Eiseman
(74) *Attorney, Agent, or Firm* — Pandiscio & Pandiscio

(57) ABSTRACT

The present invention comprises the provision and use of new and improved arthroscopic instrumentation for (i) harvesting a tissue biopsy from a non-critical section of a joint, and (ii) sizing and seating an autologous graft at an implant site.

7 Claims, 33 Drawing Sheets

3. CUT THE TEMPLATE TO SIZE AND CONFIRM FIT ARTHROSCOPICALLY

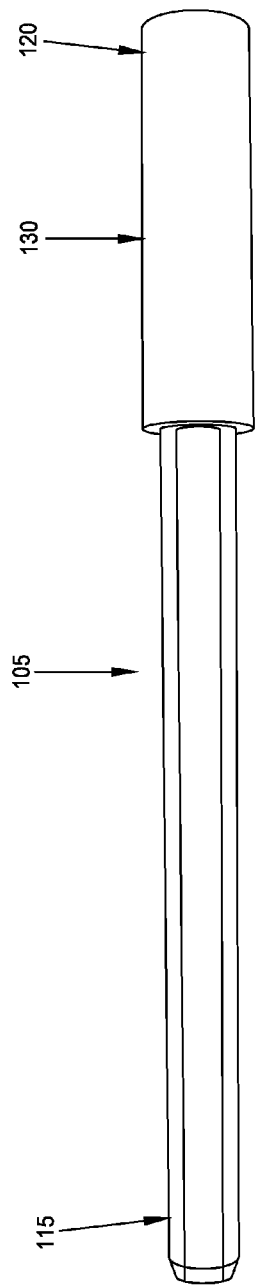
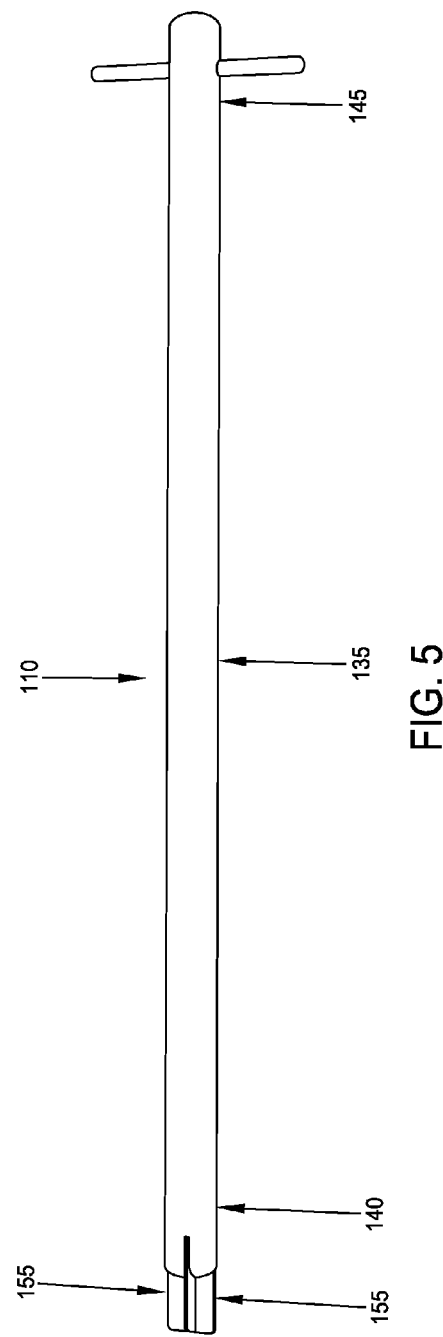
FIG. 4
FIG. 5

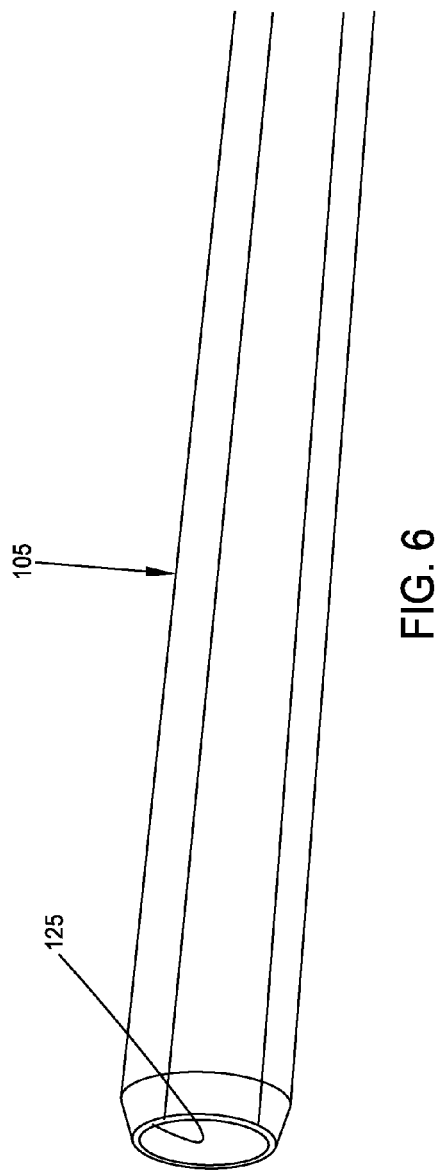
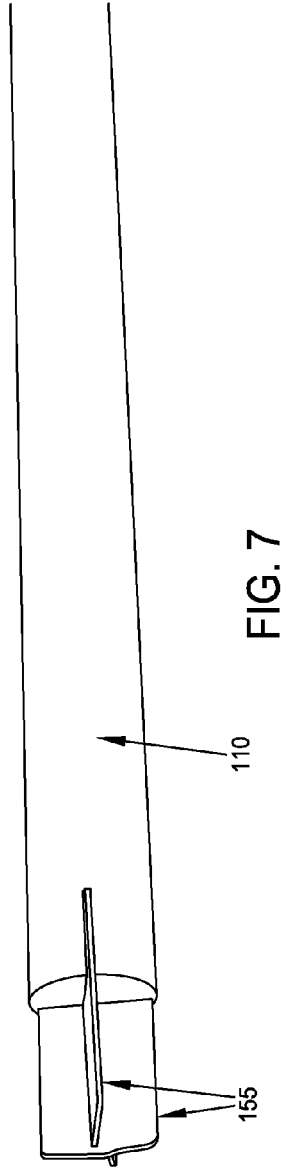

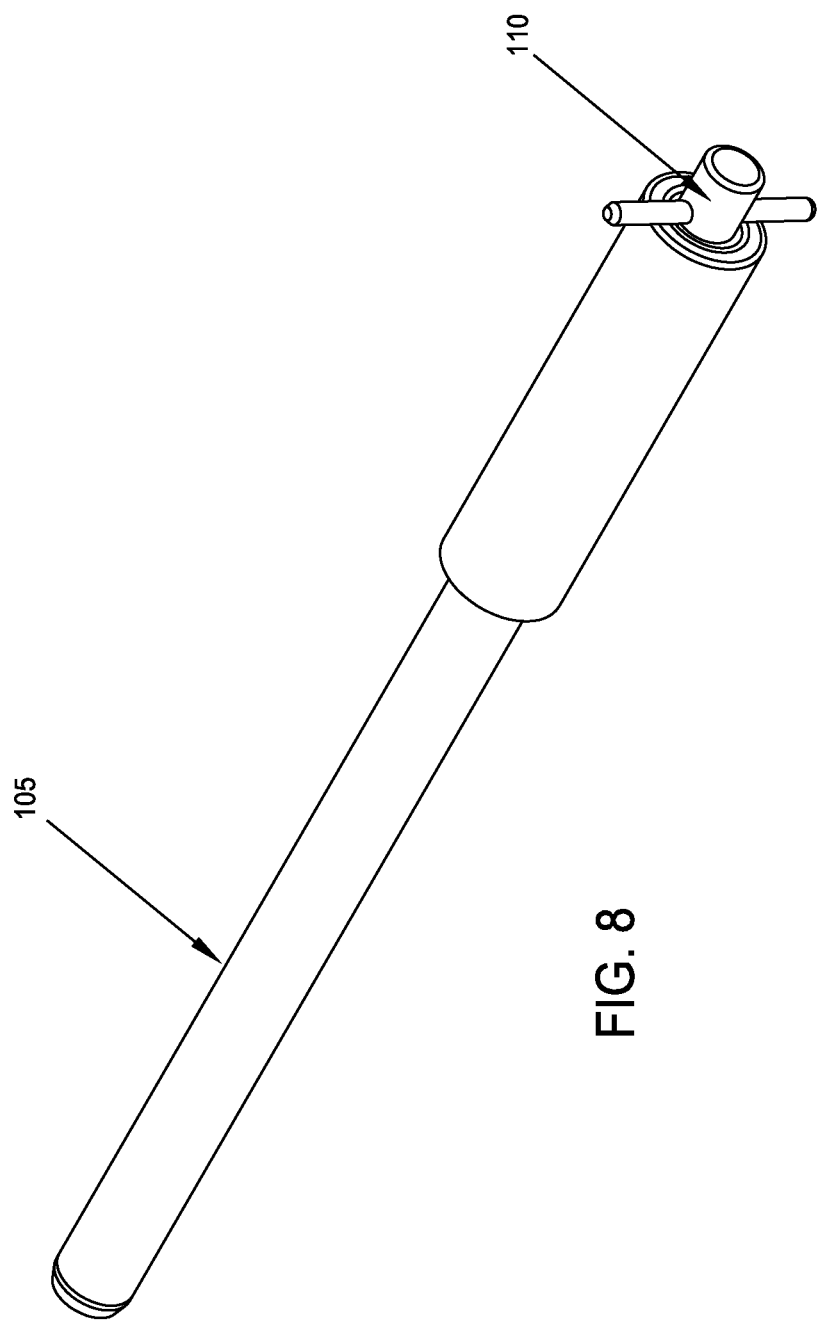

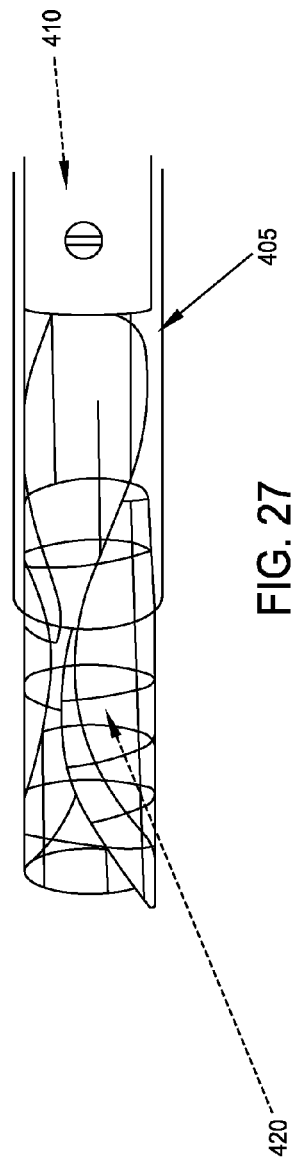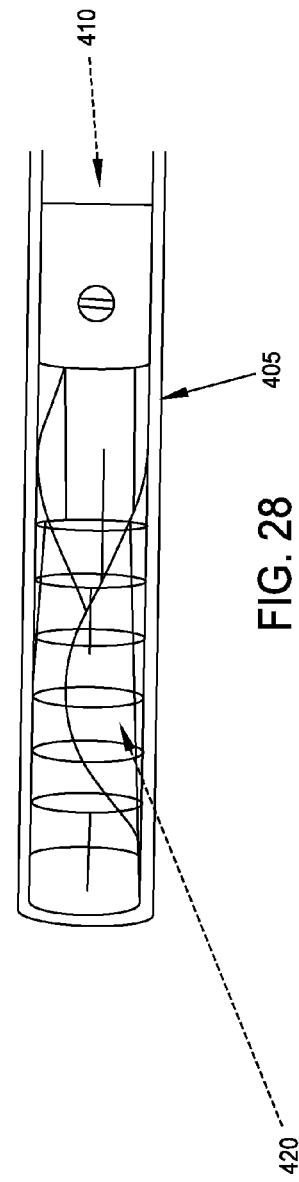

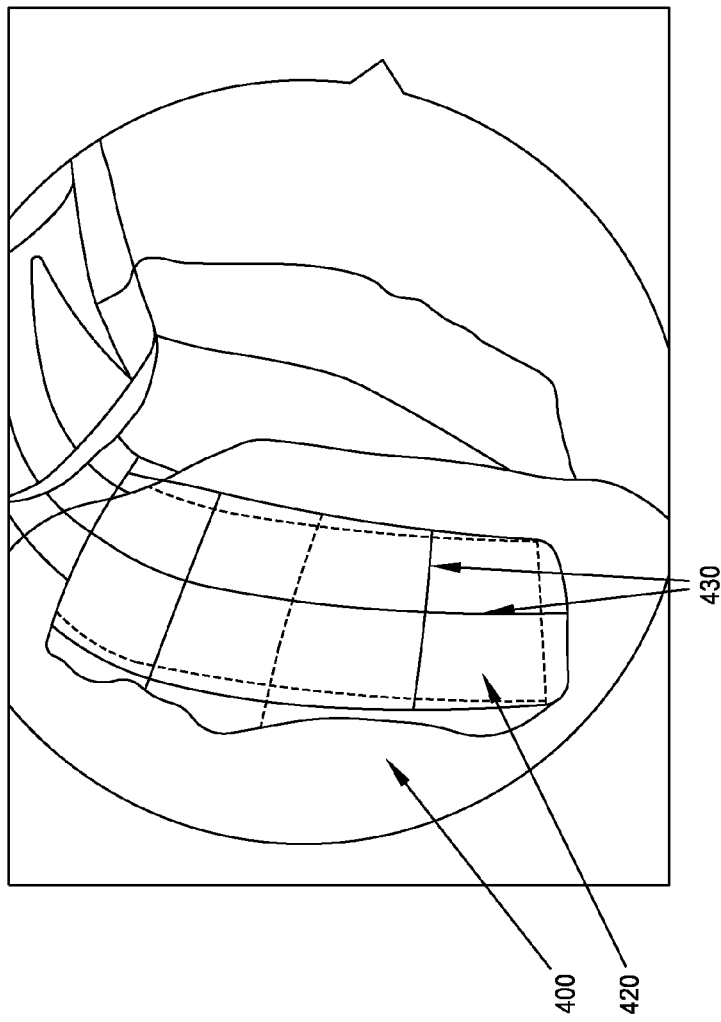

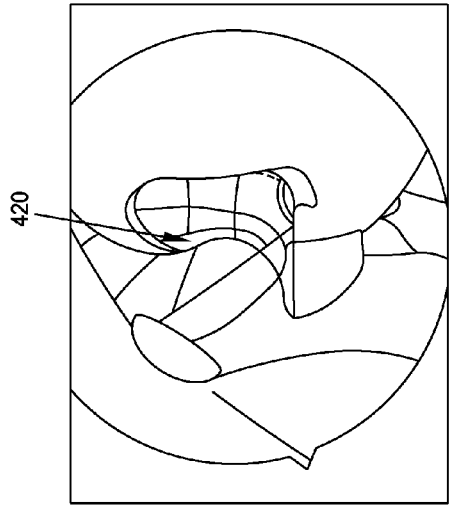
FIG. 39
5. INSERT THE AUTOLOGOUS GRAFT INTO THE DEFECT ARTHROSCOPICALLY
FIG. 40
FIG. 41
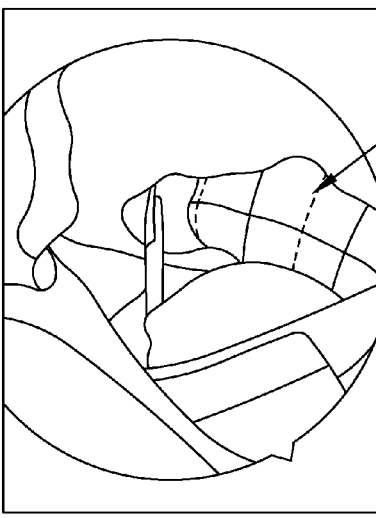
FIG. 42

METHOD AND APPARATUS FOR RESTORING ARTICULAR CARTILAGE

REFERENCE TO PENDING PRIOR PATENT APPLICATION

This patent application claims benefit of pending prior U.S. Provisional Patent Application Ser. No. 61/383,823, filed Sep. 17, 2010 by Thomas C. May et al. for METHOD AND APPARATUS FOR RESTORING ARTICULAR CARTILAGE, which patent application is hereby incorporated herein by reference.

FIELD OF THE INVENTION

This invention relates to medical apparatus and procedures in general, and more particularly to medical apparatus and procedures for restoring articular cartilage.

BACKGROUND OF THE INVENTION

Articular cartilage is a firm, rubbery tissue that covers the articulating surfaces of bones. Articular cartilage provides a smooth gliding surface for joints and acts as a cushion between adjacent bones.

Articular cartilage can break down due to overuse, injury and/or disease. This deterioration of articular cartilage can result in substantial pain and swelling for the patient, and can significantly impact patient lifestyle.

Various treatments have been devised to address the deterioration of articular cartilage. In some circumstances, a plug of bone (with a segment of articular cartilage attached thereto) may be harvested from one part of the body and transplanted to another part of the body, e.g., from a non-weight-bearing section of a joint to a weight-bearing section of a joint. In other circumstances, a prosthetic device (having a smooth bearing surface formed thereon) may be installed in place of the deteriorated articular cartilage. However, the aforementioned plug transplantations, and the aforementioned prosthetic device installations, tend to suffer from a number of deficiencies, e.g., limitations on the types and sizes of cartilage defects which can be treated using these approaches, trauma to the body at the donor site in the case of plug transplantations, performance deficiencies in the case of prosthetic devices, etc.

Recent advances in in vitro cell growth has now made it possible to restore articular cartilage by means of autologous chondrocyte implantation (ACI). More particularly, with this approach, a small portion of healthy articular cartilage (sometimes referred to herein as "a tissue biopsy", or simply "a biopsy") is first harvested from a non-critical section of a joint (e.g., in the case of a knee or hip, from a non-weight-bearing section of the knee or hip). The harvested tissue biopsy is then sent to a processing laboratory where it is appropriately processed, i.e., to extract healthy chondrocyte cells from the tissue biopsy and then culture those chondrocyte cells on a carrier matrix for a period of time (e.g., several weeks) so as to produce a healthy, vibrant autologous graft. Thereafter, in a follow-up procedure, the implant site is prepared to receive the autologous graft, the autologous graft is properly sized for the implant site, and then the autologous graft is introduced into the body and seated at the implant site.

Preferably the foregoing ACI procedure is conducted as an arthroscopic (i.e., as a minimally-invasive, "keyhole surgery") procedure so as to minimize trauma to the tissue of the patient and thereby accelerate the recovery period for the patient.

While the aforementioned ACI procedure offers tremendous advantages for the patient, it currently suffers from the lack of effective arthroscopic instrumentation for (i) harvesting a tissue biopsy from a non-critical section of a joint, and (ii) sizing and seating an autologous graft at an implant site.

Thus there is a need for new and improved arthroscopic instrumentation for (i) harvesting a tissue biopsy from a non-critical section of a joint, and (ii) sizing and seating an autologous graft at an implant site.

SUMMARY OF THE INVENTION

The present invention comprises the provision and use of new and improved arthroscopic instrumentation for (i) harvesting a tissue biopsy from a non-critical section of a joint, and (ii) sizing and seating an autologous graft at an implant site.

In one preferred form of the present invention, there is provided an arthroscopic cartilage biopsy tool comprising:
an outer tube comprising a distal end, a proximal end, and a lumen extending between the distal end and the proximal end;
an inner core comprising a shaft having a distal end and a proximal end, and at least one blade mounted to the distal end of the shaft; and
the inner core being rotatably mounted within the lumen of the outer tube such that the at least one blade protrudes beyond the distal end of the outer tube.

In another preferred form of the present invention, there is provided a method for arthroscopically harvesting a tissue biopsy, the method comprising:
providing an arthroscopic cartilage biopsy tool comprising:
an outer tube comprising a distal end, a proximal end, and a lumen extending therebetween; and
an inner core comprising a shaft having a distal end and a proximal end, and at least one blade mounted to the distal end of the shaft;
the inner core being rotatably mounted within the lumen of the outer tube such that the at least one blade protrudes beyond the distal end of the outer tube;
advancing the at least one blade of the arthroscopic cartilage biopsy tool into the tissue which is to be harvested; and
rotating the inner core so as to cause the at least one blade to excise the tissue to be harvested.

In another preferred form of the present invention, there is provided an arthroscopic suction curette biopsy tool comprising:
a hollow tube having a distal end including at least one sharp edge, a proximal end, a lumen extending between the distal end and the proximal end, and a side opening extending through the side wall of the hollow tube and communicating with the lumen.

In another preferred form of the present invention, there is provided a method for arthroscopically harvesting a tissue biopsy, the method comprising:
providing an arthroscopic suction curette biopsy tool comprising:
a hollow tube having a distal end including at least one sharp edge, a proximal end, a lumen extending between the distal end and the proximal end, and a side opening extending through the side wall of the hollow tube and communicating with the lumen;
applying suction to the lumen at the proximal end of the hollow tube;
manipulating the hollow tube so that the at least one sharp edge excises the tissue which is to be harvested; and selectively blocking the side opening with a thumb or finger of the user so as to apply suction to the lumen at the distal end of the hollow tube so as to secure the excised tissue to the distal end of the hollow tube.

In another preferred form of the present invention, there is provided an arthroscopic tape measurer tool comprising:

a hollow tube having a distal end, a proximal end, and a lumen extending between the distal end and the proximal end;

a tape ribbon movably disposed within the lumen of the hollow tube, the tape ribbon having length markings thereon; and movement means for moving the tape ribbon relative to the hollow tube.

In another preferred form of the present invention, there is provided a method for arthroscopically measuring a graft site, the method comprising:

providing an arthroscopic tape measurer tool comprising:
a hollow tube having a distal end, a proximal end, and a lumen extending between the distal end and the proximal end;
a tape ribbon movably disposed within the lumen of the hollow tube, the tape ribbon having length markings thereon; and
movement means for moving the tape ribbon relative to the hollow tube;

manipulating the movement means so that the tape ribbon is withdrawn into the interior of the hollow tube;

advancing the distal end of the hollow tube so that it resides adjacent to a graft site;

manipulating the movement means so that the tape ribbon is extended out of the distal end of the hollow tube; and using the length markings formed on the tape ribbon to measure the graft site.

In another preferred form of the present invention, there is provided an arthroscopic applicator tool and measuring template comprising:

an outer tube having a distal end, a proximal end, and a lumen extending between the distal end and the proximal end; and an inner rod comprising a shaft having a distal end and a proximal end, and a measuring template mounted to the distal end of the shaft;

the inner rod being movably mounted within the lumen of the outer tube such that the distal end of the inner rod can project out the distal end of the outer tube or be withdrawn into the lumen of the outer tube; and the measuring template being foldable along its longitudinal axis so that the measuring template can be received within the interior of the outer tube.

In another preferred form of the present invention, there is provided a method for arthroscopically measuring objects and for applying an autologous graft to the anatomy of a patient, the method comprising:

providing an arthroscopic applicator tool and measuring template comprising:
an outer tube having a distal end, a proximal end, and a lumen extending between the distal end and the proximal end; and
an inner rod comprising a shaft having a distal end and a proximal end, and a measuring template mounted to the distal end of the shaft;
the inner rod being movably mounted within the lumen of the outer tube such that the distal end of the inner rod can project out the distal end of the outer tube or be withdrawn into the lumen of the outer tube; and
the measuring template being foldable along its longitudinal axis so that the measuring template can be received within the interior of the outer tube;

positioning the measuring template within the outer tube;
advancing the distal end of the outer tube to an interior site; and
advancing the measuring template out of the outer tube and using the measuring template to measure an object at an interior site.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts and further wherein:

FIGS. 2-13 are schematic views showing the multi-blade cartilage biopsy tool shown in FIG. 1;

FIGS. 24-31 are schematic views showing a novel arthroscopic applicator tool and measuring template for sizing and seating an autologous graft at an implant site; and FIGS. 32-44 are schematic views showing selected steps from an exemplary procedure for harvesting a tissue biopsy from a non-critical section of a joint, and sizing and seating an autologous graft at the implant site, using the novel instrumentation of the present invention.

DESCRIPTION OF THE PREFERRED EMBODIMENTS

The present invention comprises the provision and use of new and improved arthroscopic instrumentation for (i) harvesting a tissue biopsy from a non-critical section of a joint, and (ii) sizing and seating an autologous graft at an implant site.

1. Novel Arthroscopic Instrumentation for Harvesting a Tissue Biopsy from a Non-Critical Section of a Joint The present invention comprises the provision and use of new and improved arthroscopic instrumentation ("cartilage biopsy tools") for harvesting a tissue biopsy from a non-critical section of a joint.

Figure 1:
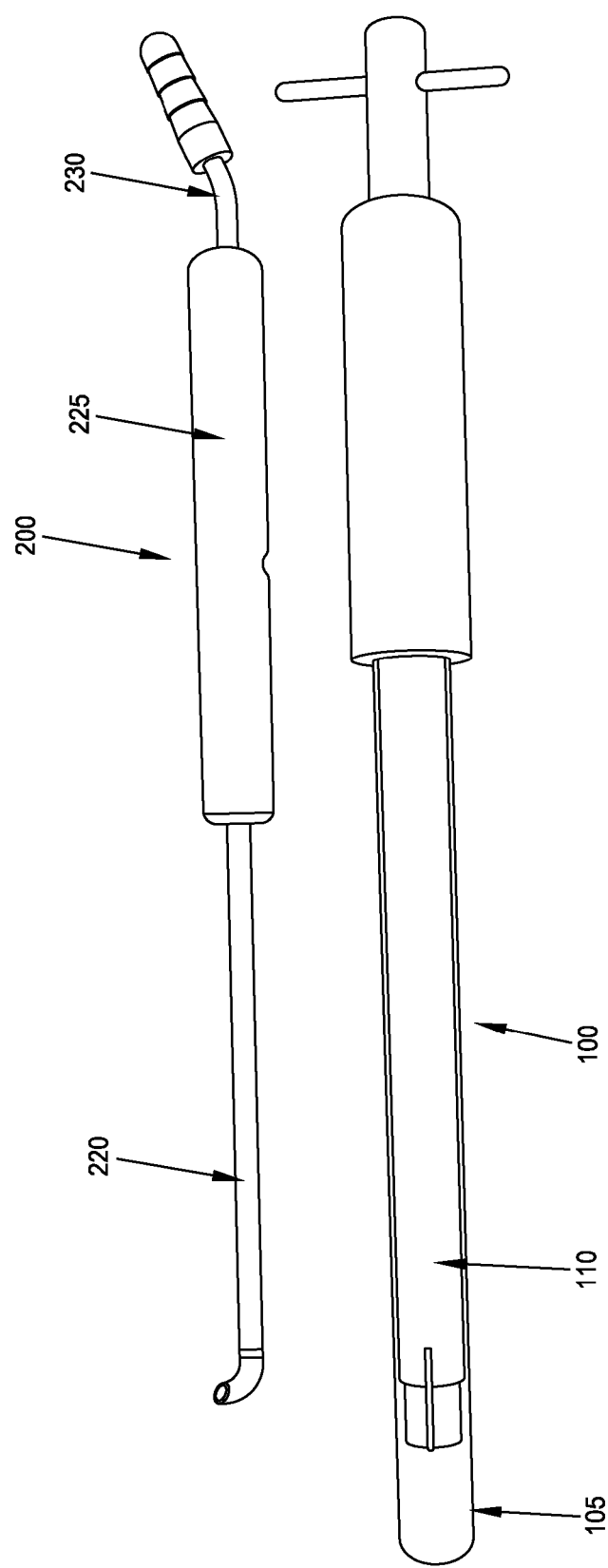
FIG. 1 is a schematic view showing novel arthroscopic instrumentation for harvesting a tissue biopsy from a non-critical section of a joint.
Figure 2:
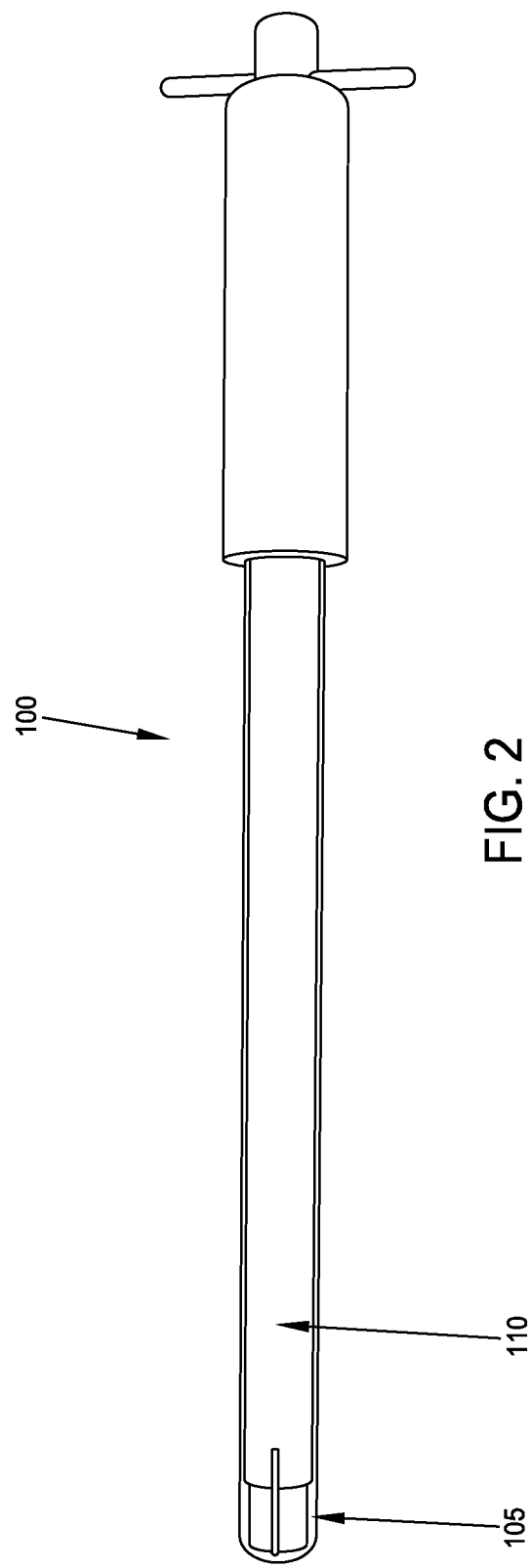
Figure 3:
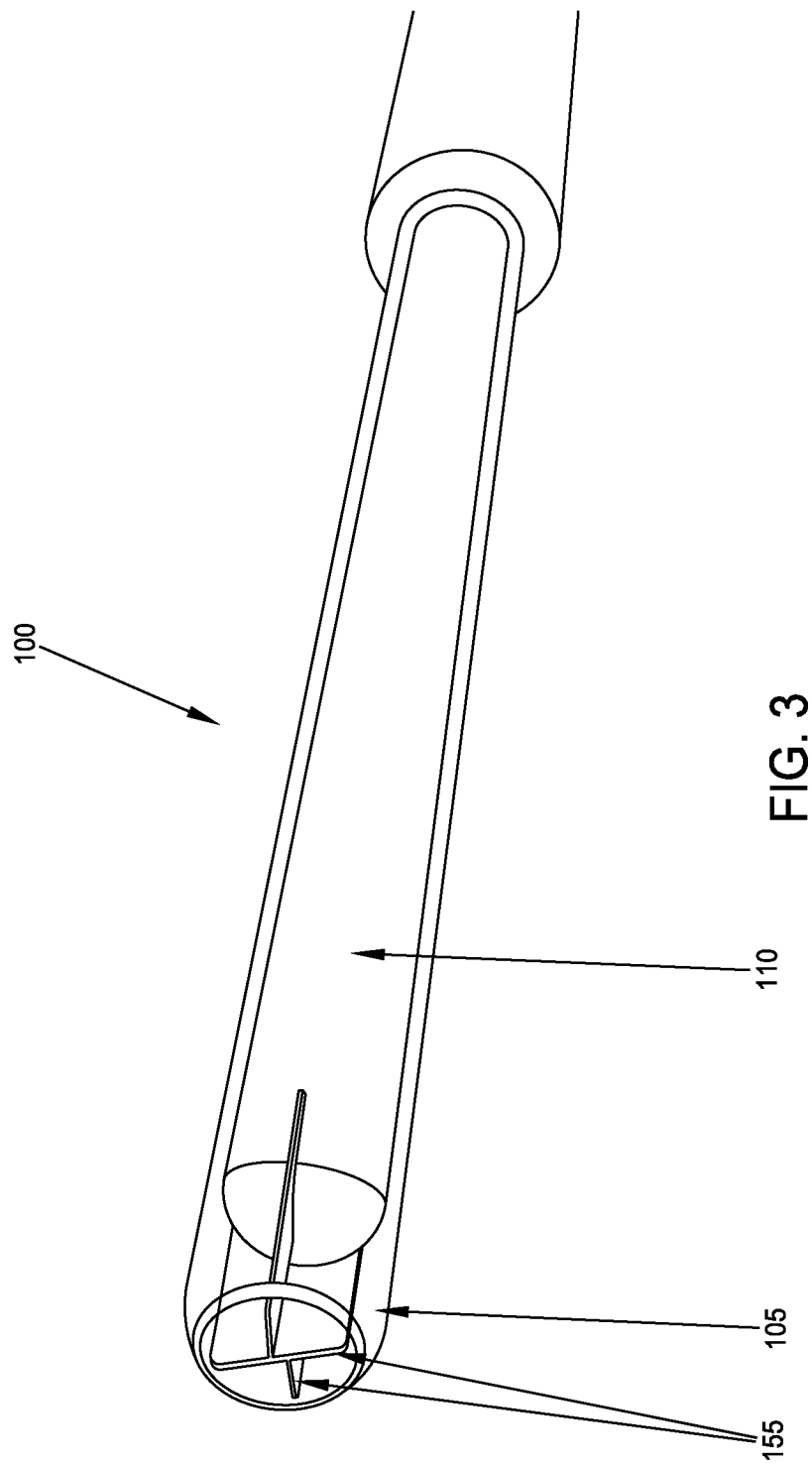
Figure 9:
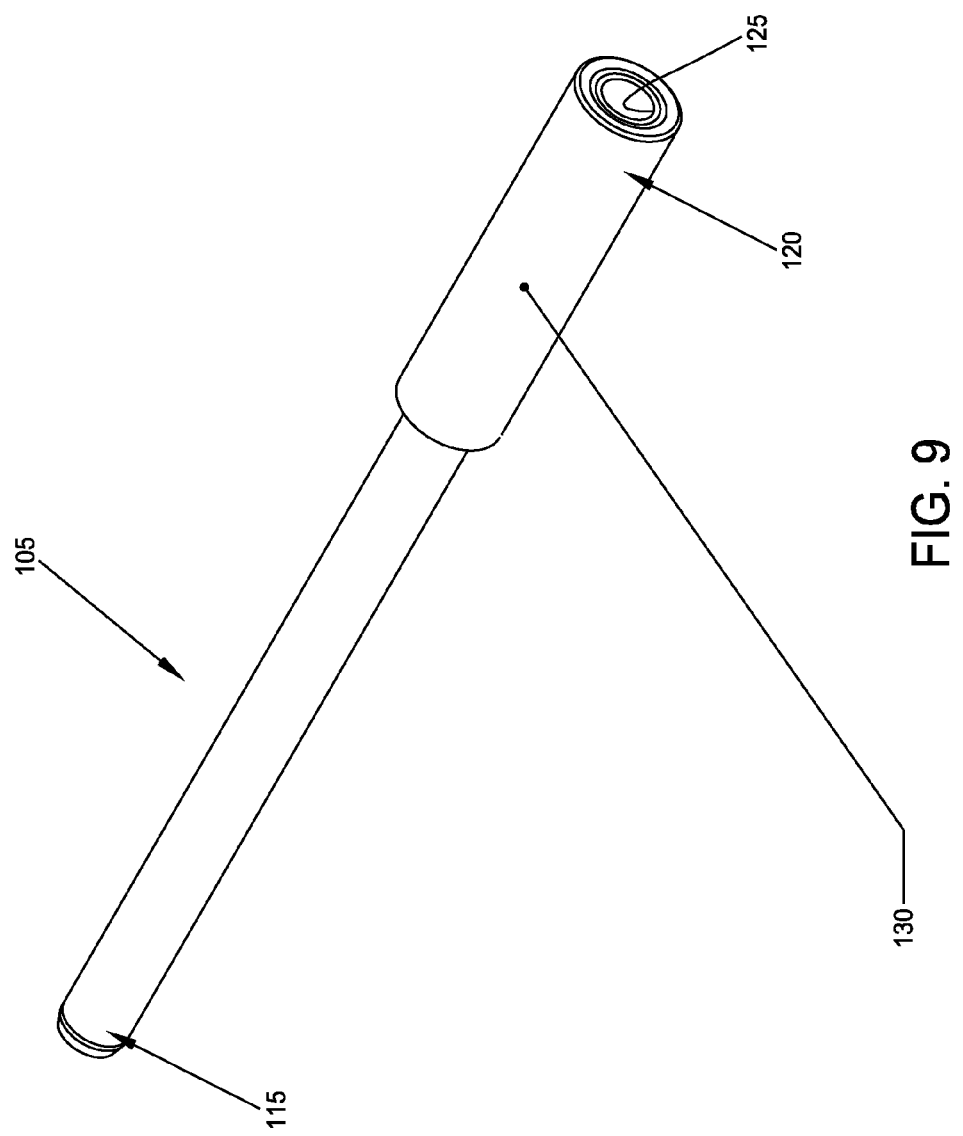
Figure 10:
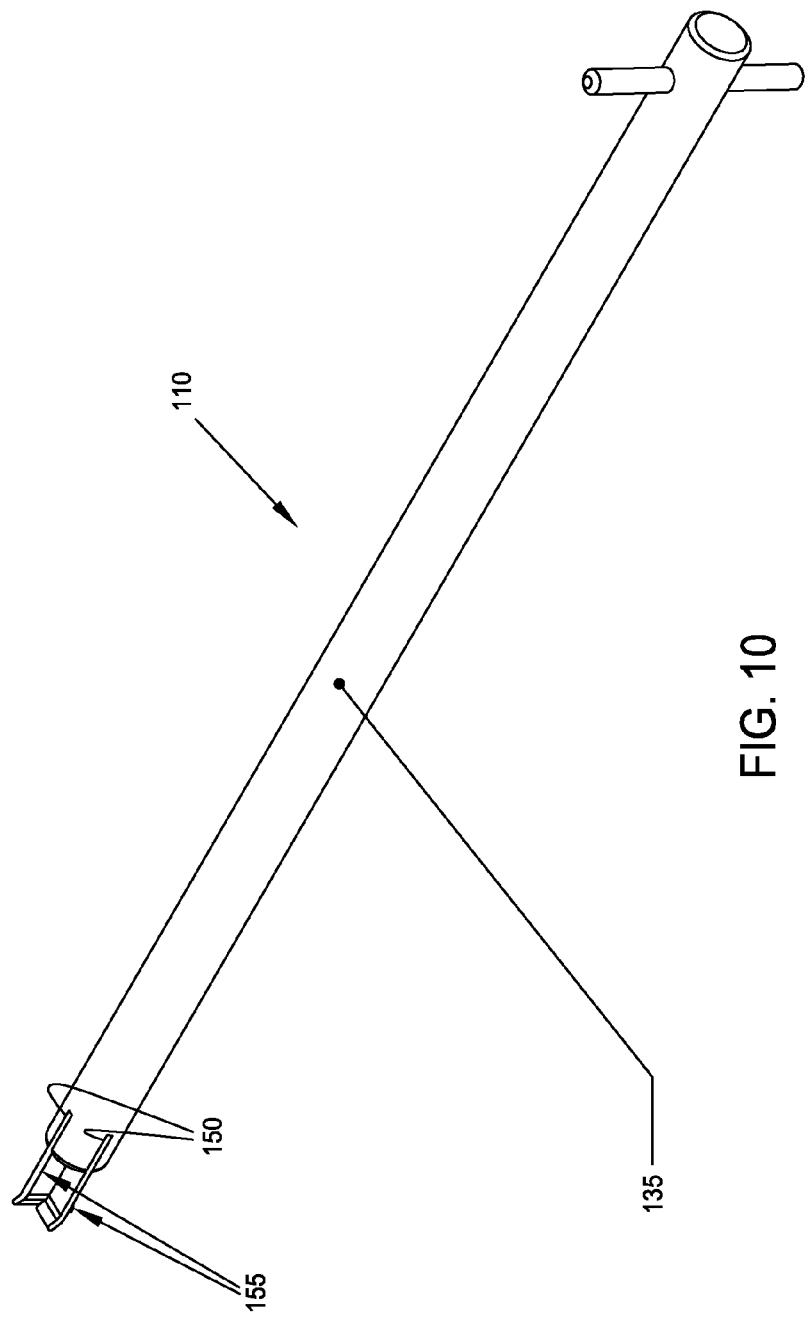

In one preferred form of the invention, and looking now at FIG. 1, two novel cartilage biopsy tools are provided: a novel multi-blade cartilage biopsy tool 100, and a novel suction curette biopsy tool 200.

(i) Multi-Blade Cartilage Biopsy Tool 100 for Harvesting a Tissue Biopsy

Multi-blade cartilage biopsy tool 100 is shown in detail in FIGS. 2-13. Multi-blade cartilage biopsy tool 100 generally comprises an outer tube 105 and an inner core 110.

More particularly, outer tube 105 generally comprises a distal end 115, a proximal end 120 and a lumen 125 extending therebetween. If desired, proximal end 120 of outer tube 105 may have an enlarged diameter (e.g., as shown at 130) relative to the remainder of the outer tube so as to provide a more convenient handle for multi-blade cartilage biopsy tool 100.

In one preferred form of the invention, at least the distal end of hollow tube 105 is transparent.

Figure 11:
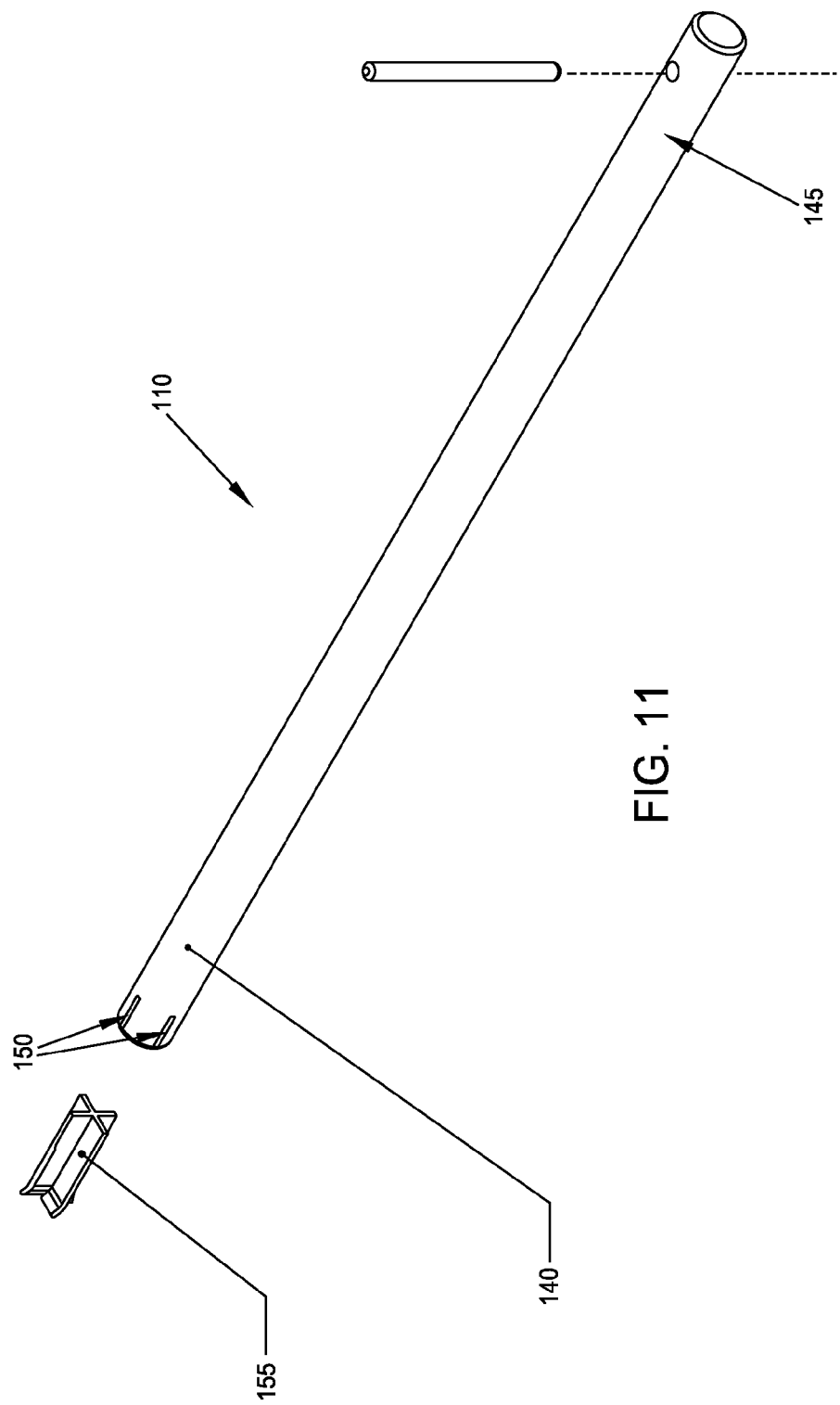
Figure 12:
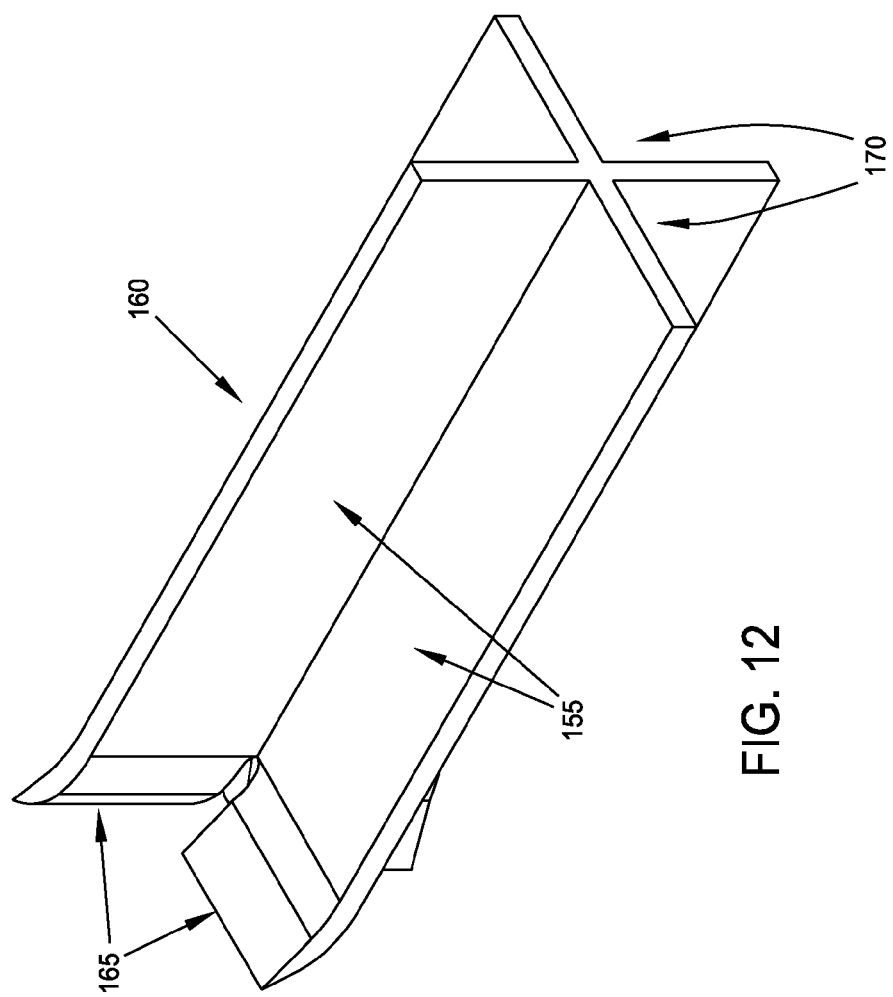
Figure 13:
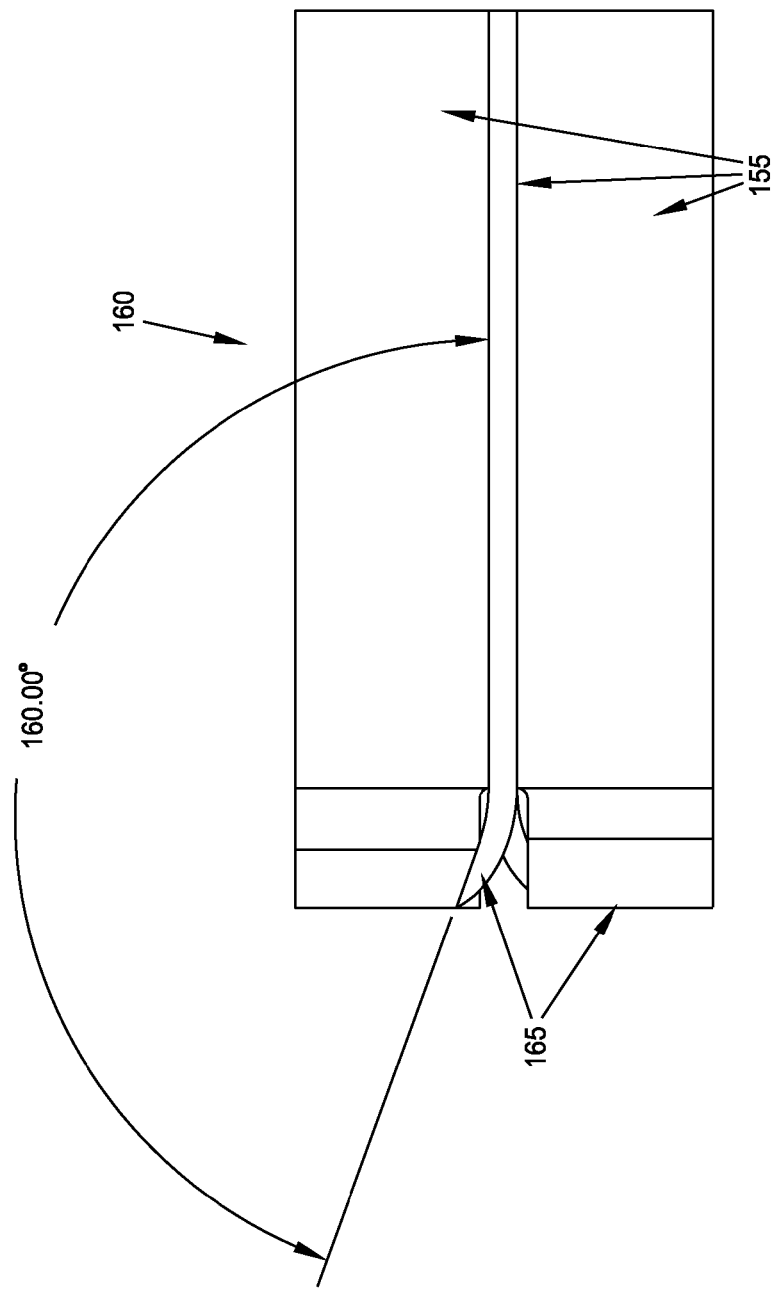
Figure 14:
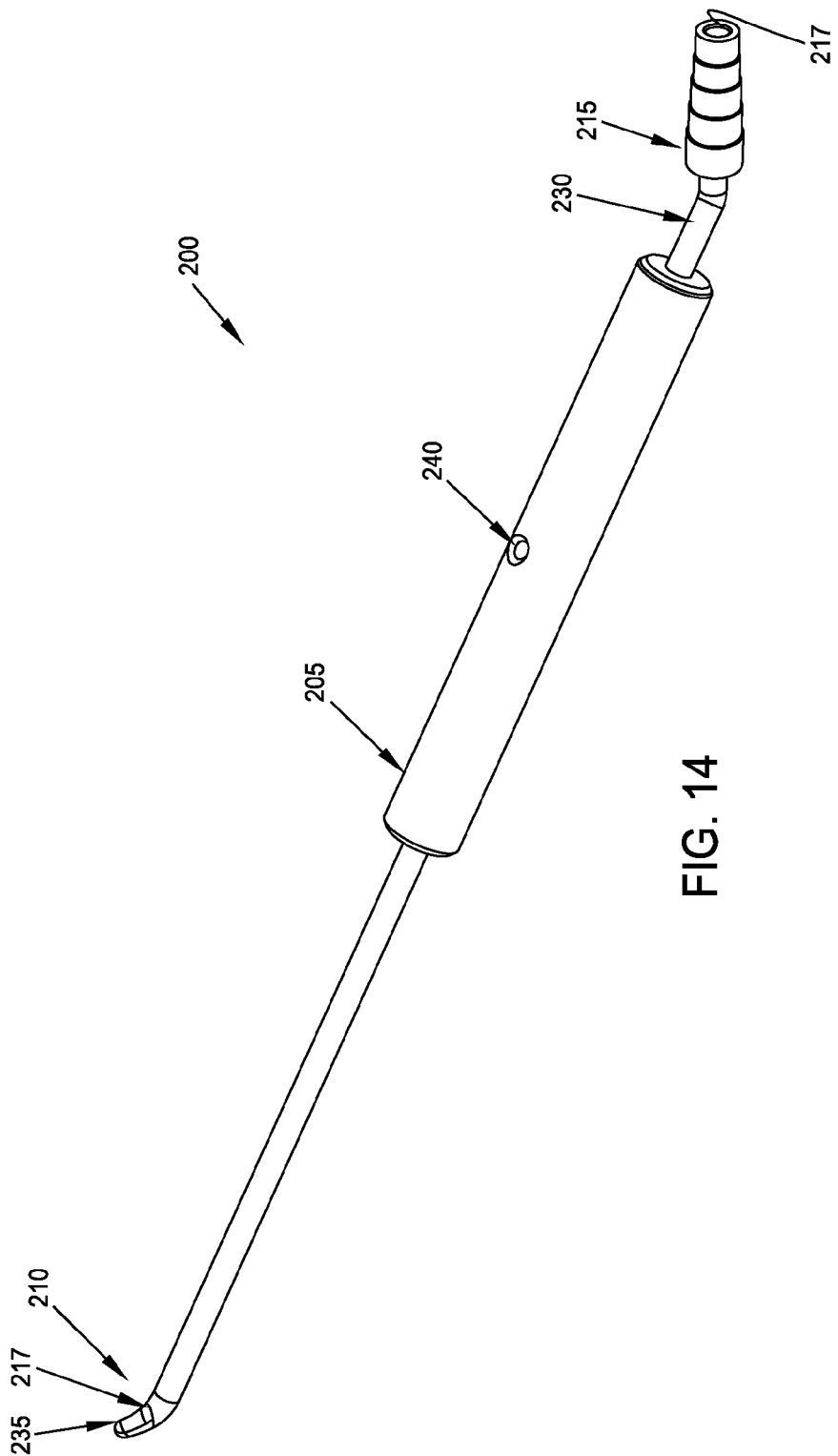
FIGS. 14-18 are schematic views showing the suction curette biopsy tool shown in FIG. 1.
Figure 15:
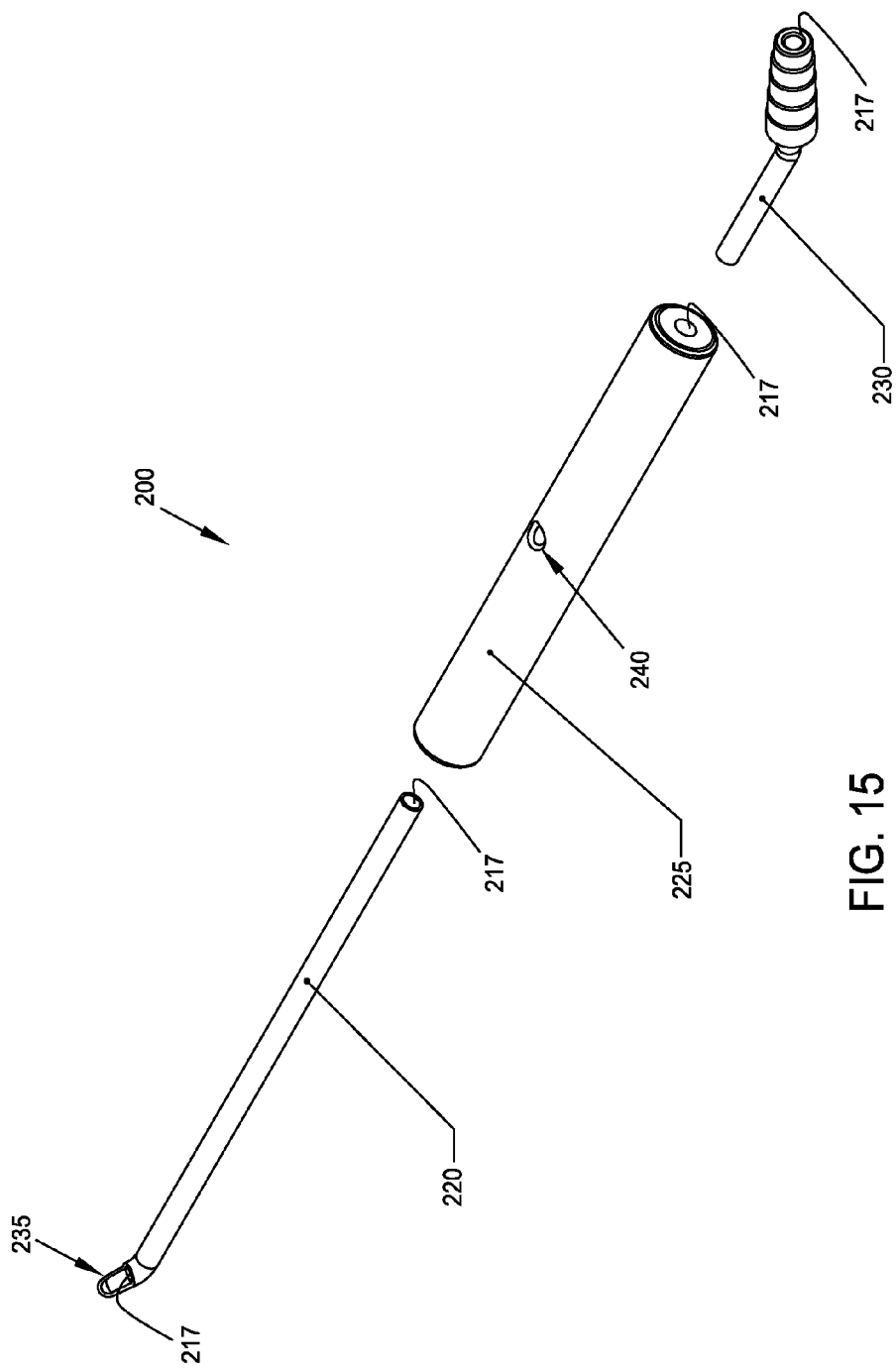
Figure 16:
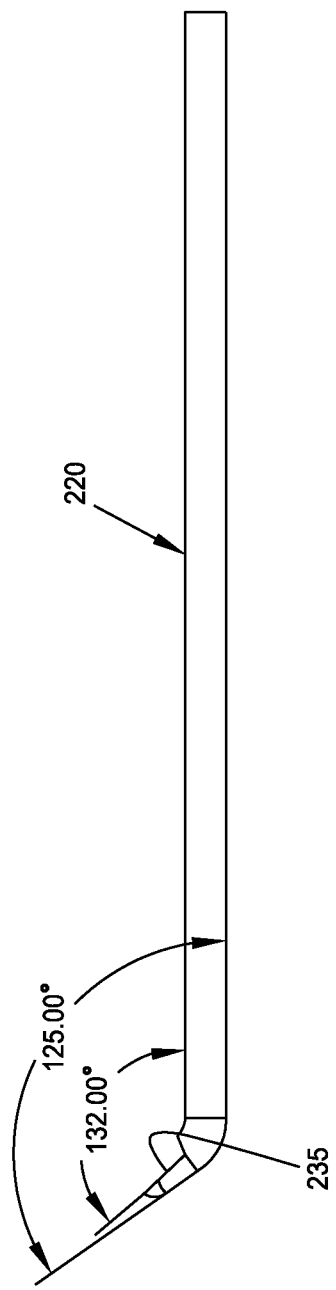
Figure 17:
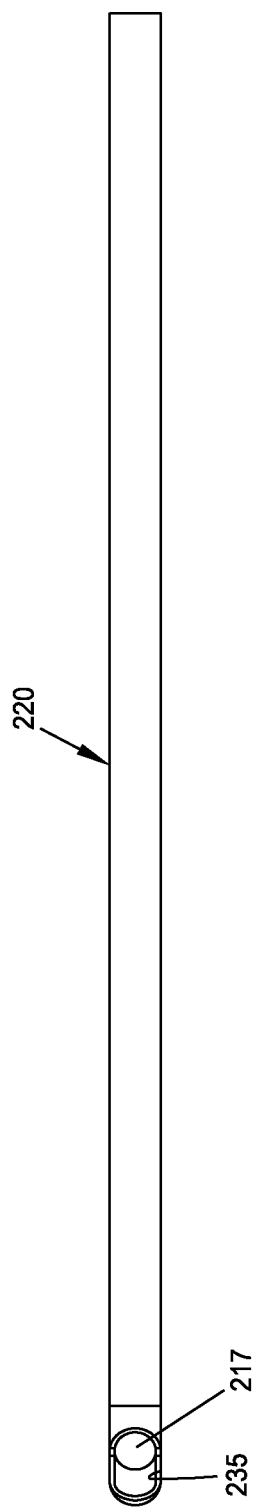
Figure 18:
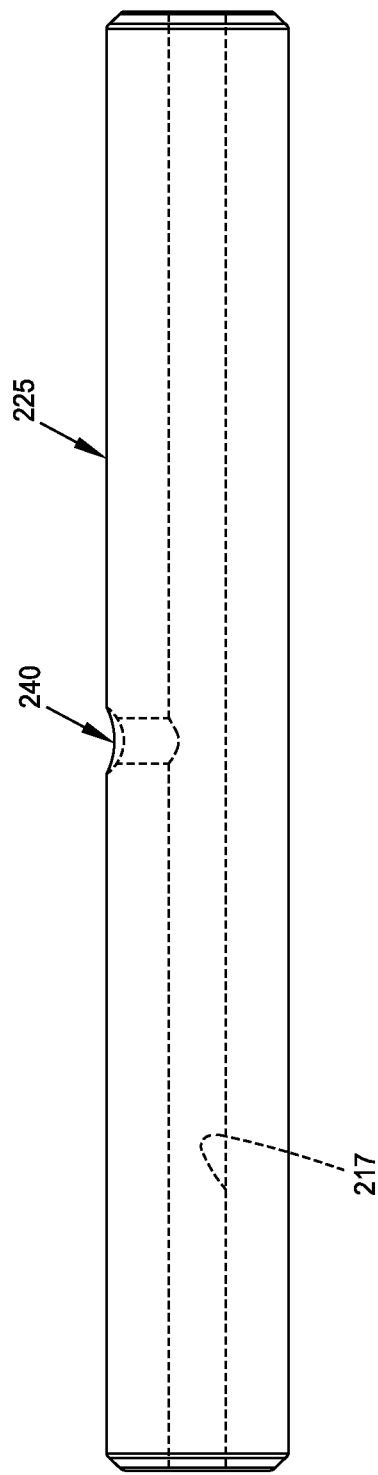
Figure 19:
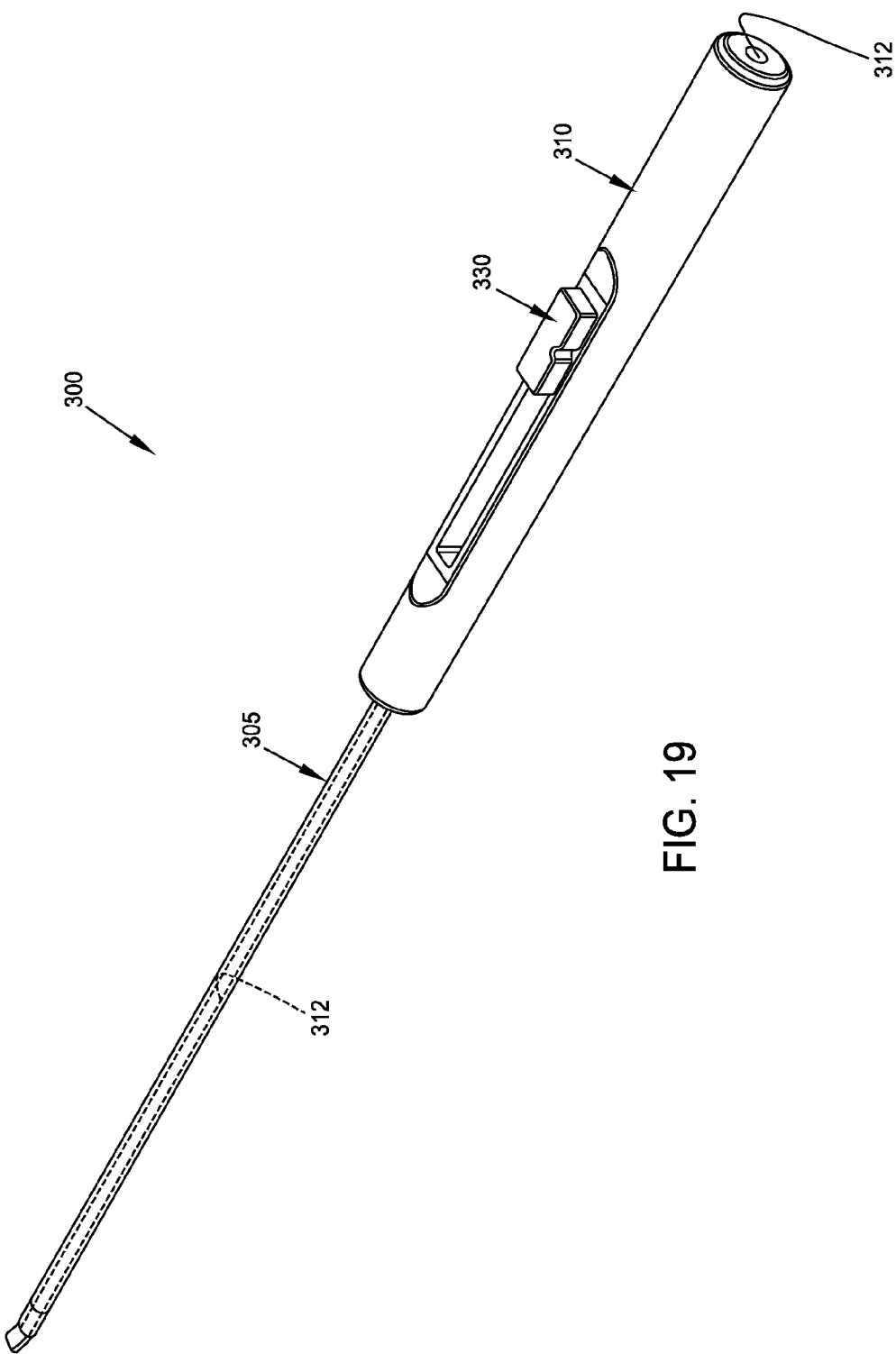
FIGS. 19-23 are schematic views showing a novel arthroscopic tape measurer tool which may be used to size an autologous graft for an implant site.
Figure 20:
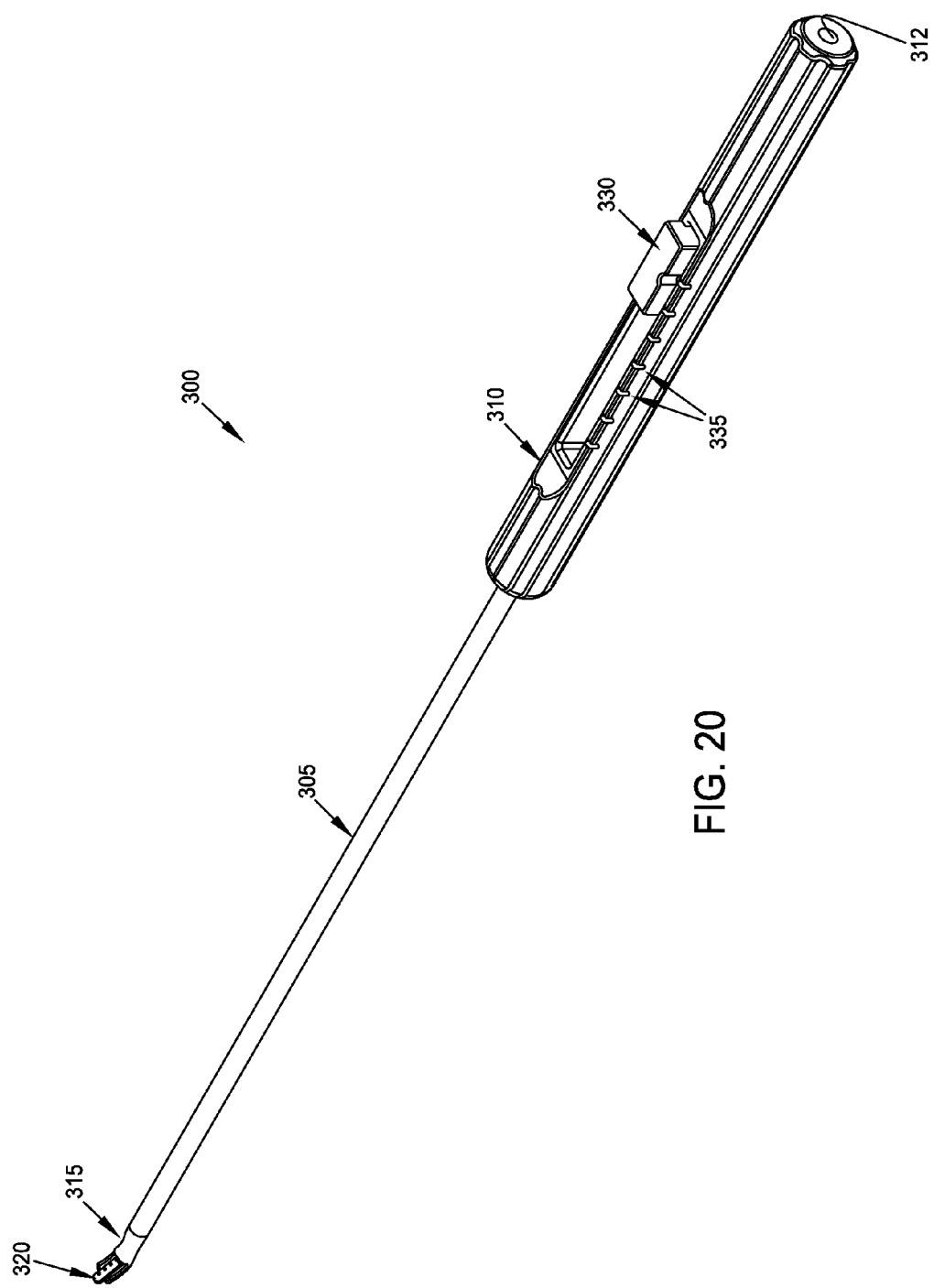
Figure 21:
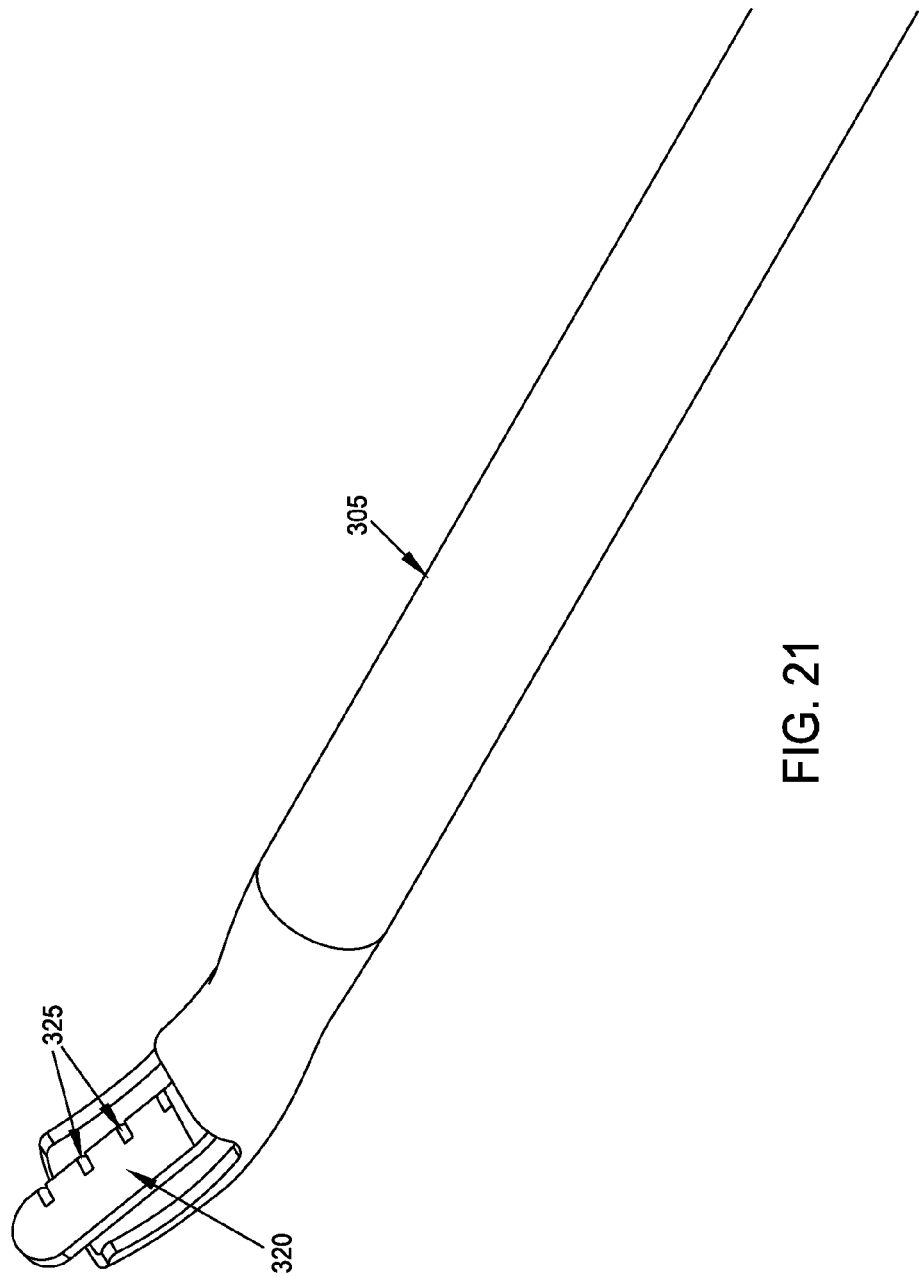
Figure 22:
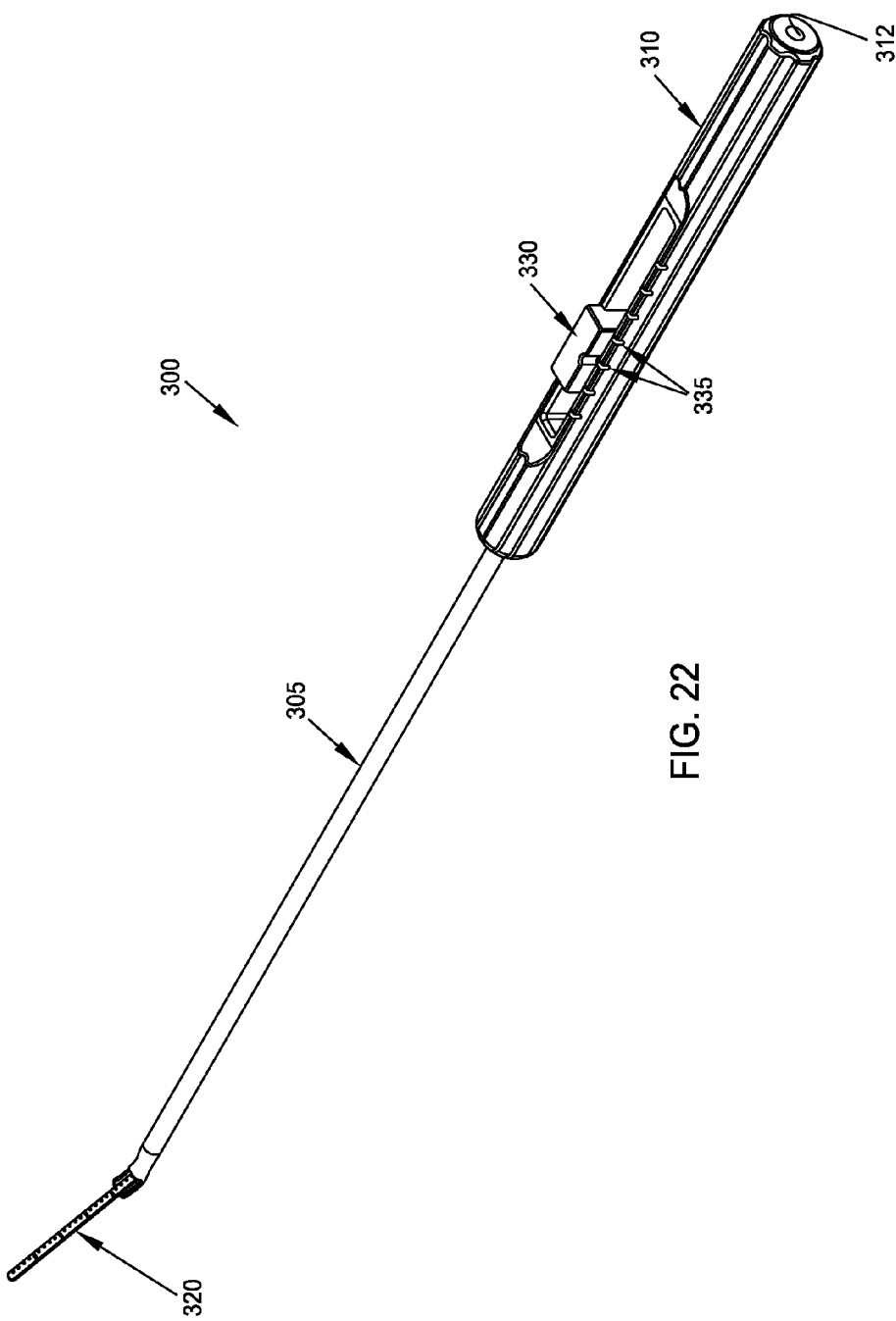
Figure 23:
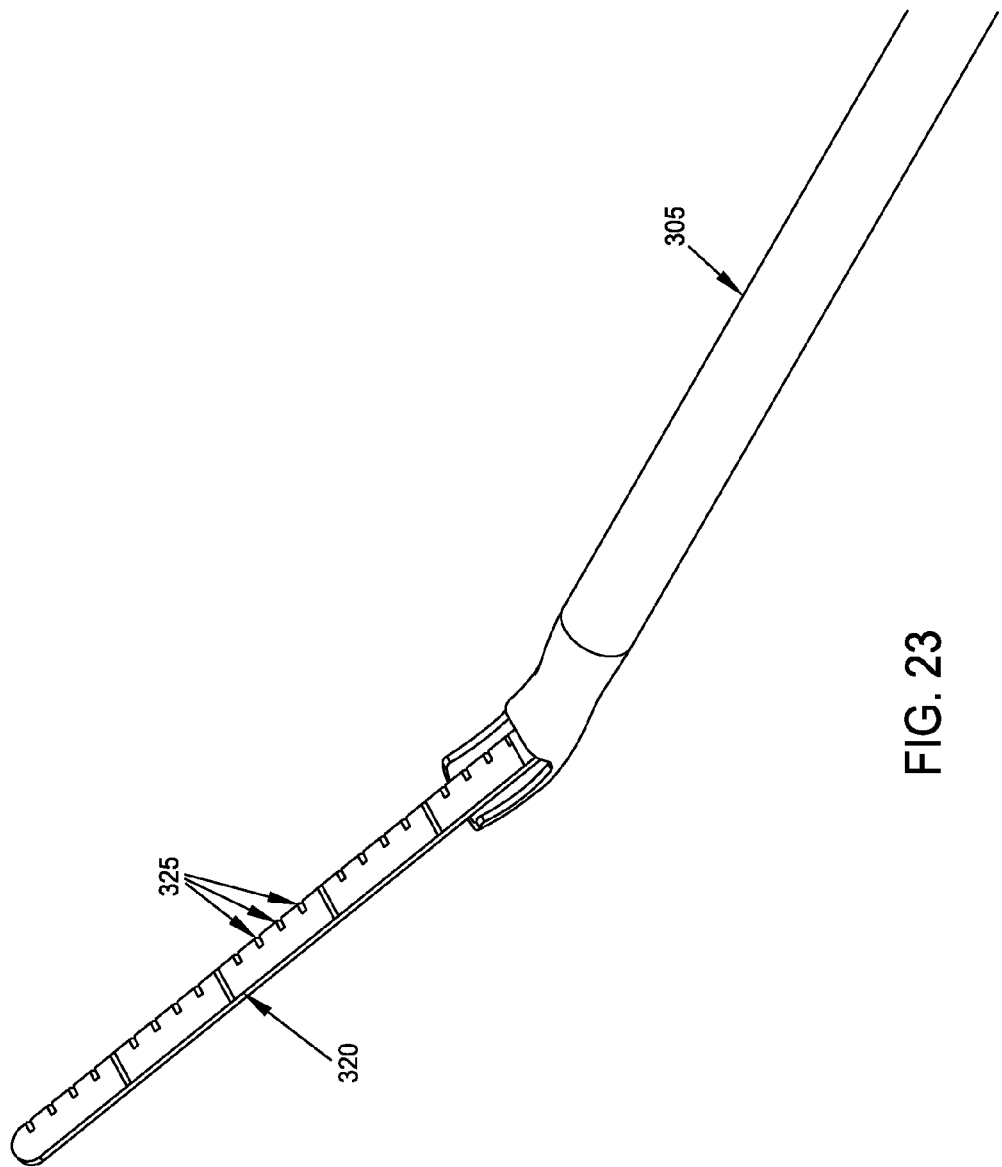
Figure 24:
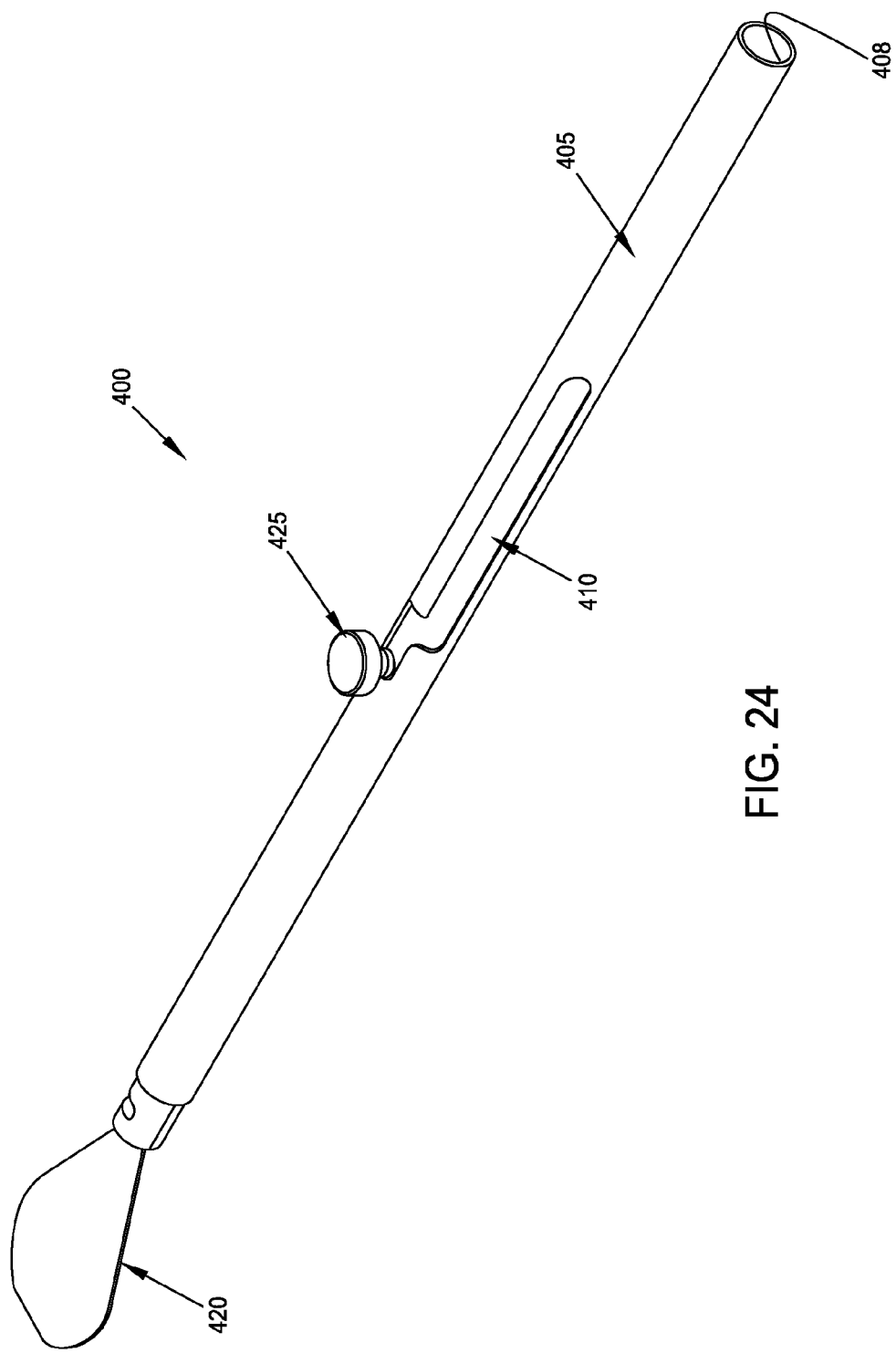
Figure 25:
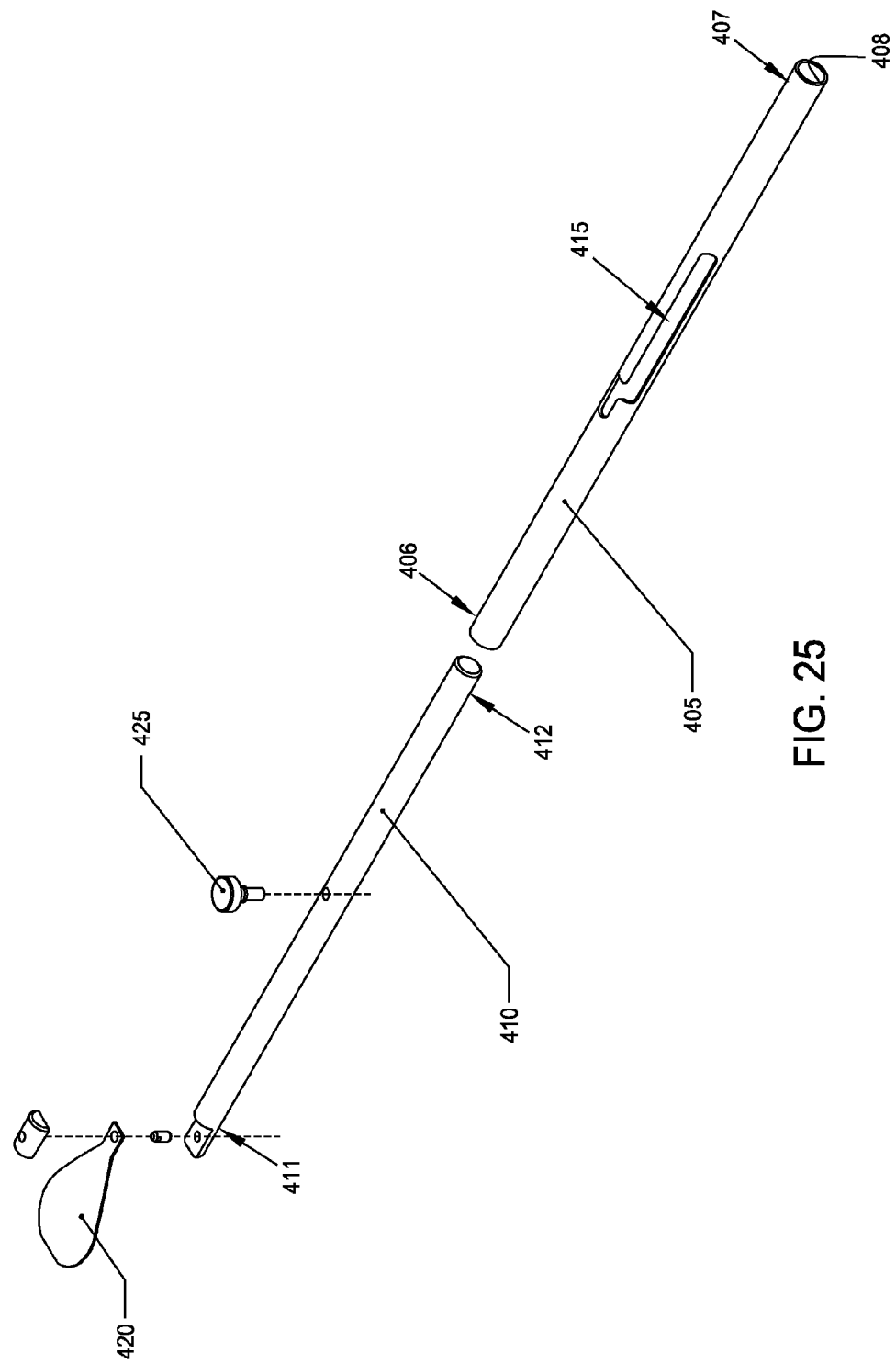
Figure 26:
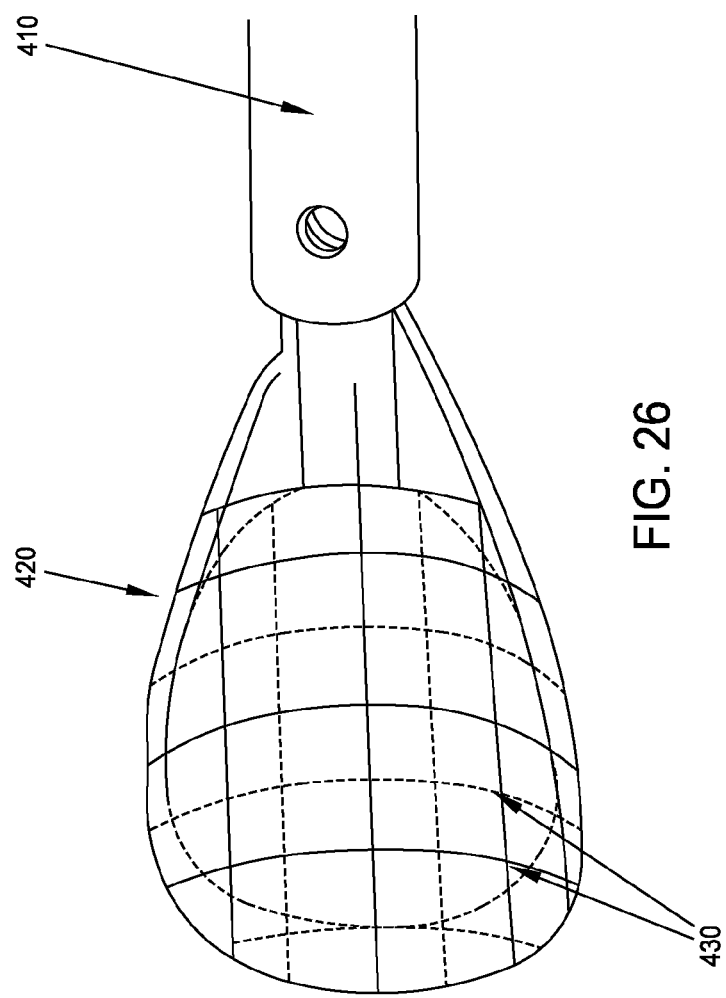
Figure 29:
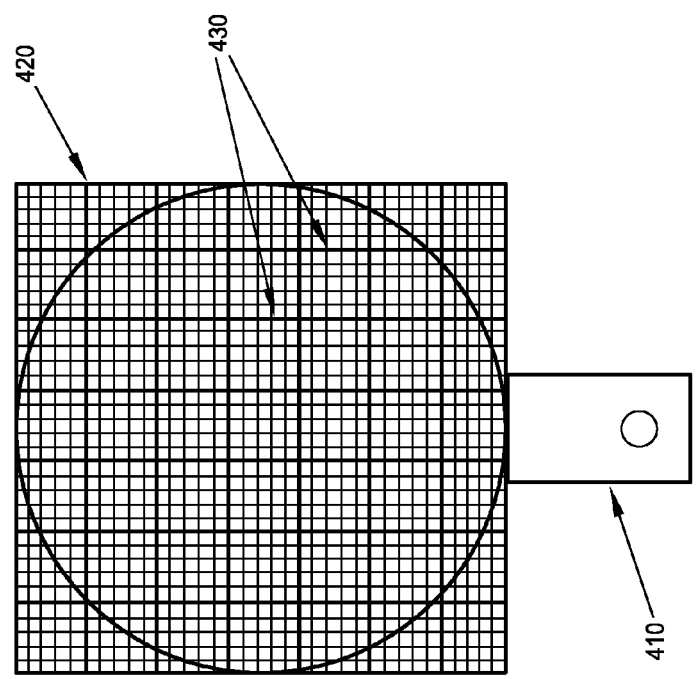
Figure 30:
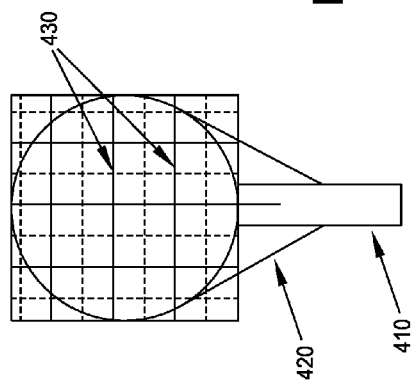
Figure 31:
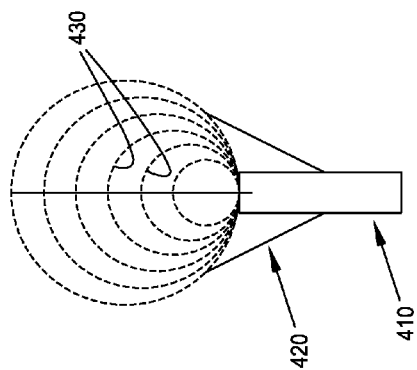

Inner core 110 generally comprises a shaft 135 having a distal end 140 and a proximal end 145. A plurality of radially-extending slits 150 are formed in distal end 140 of shaft 135. Slits 150 receive blades 155 so as to mount blades 155 to the distal end 140 of shaft 135. In one preferred form of the invention, and as shown in FIGS. 11-13, blades 155 are secured to one another so as to form a single element 160, whereby to facilitate securing blades 155 to the distal end of shaft 135 via slits 150. In one preferred form of the invention, there are four blades 155, and the blades are set at right angles to one another. Preferably each of the blades 155 has an angled distal end 165 in order to facilitate biopsy harvesting when the blades are advanced into articular cartilage and rotated, as will hereinafter be discussed in further detail. In this respect it should also be appreciated that the angled distal ends 165 of blades 155 also serve to help capture tissue fragments in the hollow receiving spaces 170 formed between the blades after the biopsy tissue has been cut away from the donor site by the blades.

Inner core 110 is rotatably mounted within lumen 125 of outer tube 105 so that blades 155 of inner core 110 protrude slightly beyond the distal end of outer tube 105, in order that blades 155 can engage and excise articular cartilage from a biopsy site, whereby to harvest a tissue biopsy. Preferably blades 155 protrude beyond the distal end of outer tube 105 by a distance which is approximately equal to the thickness of the articular cartilage which is to be harvested, in order to facilitate harvesting the desired articular cartilage without also taking significant amounts of the underlying host bone.

In use, multi-blade cartilage biopsy tool 100 is arthroscopically advanced to a donor site at a non-critical section of a joint so that the distal end of the multi-blade cartilage biopsy tool is adjacent to the donor site. Then multi-blade cartilage biopsy tool 100 is advanced distally so that blades 155 penetrate the articular cartilage. Such distal advancement continues until the distal end of outer tube 105 engages the outer surface of the articular cartilage, whereupon distal movement is stopped. At this point the distal ends of blades 155 should approximately reach the bony interface between the articular cartilage (which is to be harvested) and the host bone (which is not intended to be harvested). Then inner core 110 is rotated so that blades 155 excise the tissue biopsy from the donor site and store the tissue biopsy within lumen 125 of outer tube 105 (e.g., in the hollow receiving spaces 170 formed between the blades 155). Preferably such tissue harvesting is conducted under direct visualization using an endoscope, with the transparent distal end of outer tube 105 allowing the surgeon to observe the harvested tissue being stored within outer tube 105. At this point multi-blade cartilage biopsy tool 100 is withdrawn from the donor site, and then the harvested tissue biopsy (i.e., articular cartilage) is withdrawn from multi-blade cartilage biopsy tool 100 for transportation to a processing laboratory where the autologous graft is created from the harvested tissue biopsy.

Multi-blade cartilage biopsy tool 100 preferably harvests the tissue biopsy while the joint is being irrigated with fluid (e.g., saline), although such harvesting may also be effected in the absence of irrigation.

(ii) Suction Curette Biopsy Tool 200 for Harvesting a Tissue Biopsy

Suction curette biopsy tool 200 is shown in detail in FIGS. 14-18. Suction curette biopsy tool 200 generally comprises a hollow tube 205 having an angled distal end 210 adapted to harvest tissue, a proximal end 215 adapted for connection to a source of suction, and a lumen 217 extending therebetween.

In one preferred form of the present invention, hollow tube 205 comprises three separate elements which are integrated together so as to form the composite hollow tube 205: a distal tube 220, an intermediate tube 225 and a proximal tube 230, with the three tubes being connected to one another so as to provide a substantially rigid structure having the continuous lumen 217 extending therethrough. Angled distal end 210 includes sharpened edges 235 about some or all of its perimeter so as to allow the angled distal end to mechanically separate the desired tissue biopsy from its surrounding bone at the donor site. A side opening 240 extends through the side wall of the tool (e.g., through intermediate tube 225) and connects to continuous lumen 217 extending through hollow tube 205, whereby to allow the user to control the magnitude of the suction applied at the distal end of the tool, e.g., by selectively blocking side opening 240 with a thumb or finger, different levels of suction can be applied to the distal end of the tool. By way of example but not limitation, by completely blocking off side opening 240 with a thumb or finger, substantially full suction can be applied to the distal end of the tool.

In use, proximal end 215 of suction curette biopsy tool 200 is connected to a source of suction and, with side opening 240 uncovered so that little or no suction is applied to distal end 210 of the tool, the distal end of suction curette biopsy tool 200 is arthroscopically advanced to a donor site at a non-critical section of the joint. Then distal end 210 of the suction curette biopsy tool is brought into engagement with the donor site, and the sharpened edges 235 at the distal end of the tool are used to mechanically excise the desired tissue biopsy (i.e., articular cartilage) from the surrounding host bone. Then side opening 240 is blocked (e.g., by the thumb of the user) so that suction is transmitted to the distal end of the tool. As a result, the tissue biopsy excised by sharpened edges 235 is pulled (by suction) against the distal end of the tool. Preferably the size of the opening 210 at the distal end of the tool is coordinated with the level of suction applied to the proximal end of the tool so as to apply a level of suction to the tissue biopsy which is adequate to hold the excised tissue biopsy against the tool without damaging the tissue biopsy or drawing the tissue biopsy too far into the lumen 217 of the tool. Then, with suction being maintained at the distal end of the tool, suction curette biopsy tool 200 is withdrawn from the donor site. Thereafter, the tissue biopsy is released from the suction curette biopsy tool (e.g., by terminating the suction, and/or by replacing the suction with positive fluid pressure) and transported to a processing laboratory where the autologous graft is created from the harvested tissue biopsy.

Suction curette biopsy tool 200 preferably harvests the tissue biopsy while the joint is being irrigated with fluid (e.g., saline), although such harvesting may also be effected in the absence of irrigation.

2. Novel Arthroscopic Instrumentation for Sizing and Seating an Autologous Graft at an Implant Site The present invention also comprises the provision and use of new and improved arthroscopic instrumentation for sizing and seating an autologous graft at an implant site.

In one preferred form of the invention, two arthroscopic instruments are provided to facilitate sizing and/or seating an autologous graft at an implant site: an arthroscopic tape measurer tool 300 (FIGS. 19-23) and an arthroscopic applicator tool and measuring template 400 (FIGS. 24-31).

(i) Arthroscopic Tape Measurer Tool 300

Arthroscopic tape measurer tool 300 is shown in detail in FIGS. 19-23. Arthroscopic tape measurer tool 300 generally comprises a hollow tube 305 connected to a handle 310. Hollow tube 305 has a lumen 312 extending therethrough.

The distal end 315 of hollow tube 305 is preferably angled relative to the longitudinal axis of the remainder of the hollow tube. A tape ribbon 320 is movably disposed within lumen 312 of hollow tube 305 and has size markings 325 disposed on at least its distal end. The proximal end of tape ribbon 320 is connected to a slide button 330 which is movably mounted to handle 310. It should be appreciated that, as a result of this construction, a user can selectively project the distal end of tape ribbon 320 out of the distal end of hollow tube 305 by appropriate movement of slide button 330 relative to handle 310.

In use, the distal end of tape ribbon 320 is initially withdrawn into hollow tube 305 (e.g., by appropriate movement of slide button 330 relative to handle 310), and then the distal end of arthroscopic tape measurer tool 300 is arthroscopically advanced into a joint cavity so that the distal end of the tool is located adjacent to a defect site. Next, tape ribbon 320 is advanced out the distal end of the tool (e.g., by movement of slide button 330 relative to handle 310) and then tape ribbon 320 is used to measure the size of a cartilage defect which is to be restored with an autologous graft. Measurements may be determined using the markings 325 disposed on the distal end of the tape ribbon and/or by using corresponding calibrated measurements 335 formed on handle 310 (which match the markings 325 on the distal end of the tape ribbon). In addition, if desired, the proximal end of measuring tape 320 could extend out of the proximal end of handle 310 and include corresponding calibrated measurements on the proximal end of the measuring tape (which would correspond to the markings formed on the distal end of the tape ribbon and to the markings formed on the handle). The cartilage defect size information determined using tape ribbon 320 is recorded. Then the distal end of tape ribbon 320 is retracted back into hollow tube 305 (e.g., by appropriate movement of slide button 330 relative to handle 310), and arthroscopic tape measure tool 300 is withdrawn from the implant site. The measurements which were made of the cartilage defect using arthroscopic tape measurer 300 may then be used to size the autologous graft for proper seating at the implant site.

Arthroscopic tape measurer 300 may be used to measure the size of the cartilage defect while the joint is being irrigated with fluid (e.g., saline), or it may be used to measure the size of a defect in the absence of irrigation.

(ii) Arthroscopic Applicator Tool and Measuring Template 400

Arthroscopic applicator tool and measuring template 400 is shown in FIGS. 24-31. Arthroscopic applicator tool and measuring template 400 generally comprises an outer tube 405 and an inner rod 410. Outer tube 405 comprises a distal end 406, a proximal end 407 and a lumen 408 extending therebetween. Outer tube 405 also includes a slot 415 intermediate its length. In one preferred form of the present invention, at least the distal end of outer tube 405 is transparent. Inner rod 410 comprises a distal end 411 and a proximal end 412. Inner rod 410 is movably disposed within outer tube 405 and comprises a measuring template 420 disposed at its distal end 411 and a shaft knob 425 intermediate the length of inner rod 410. Shaft knob 425 extends through slot 415 in outer tube 405 so that the disposition of inner rod 410 vis-á-vis outer tube 405 can be manipulated via shaft knob 425.

Measuring template 420 is preferably constructed out of a clear material and preferably has a measuring grid 430 printed thereon. Measuring template 420 is formed out of material which is (i) capable of folding along its longitudinal axis (FIGS. 27 and 28) so that the measuring template can be received within the interior of hollow tube 405, and (ii) provides minimal or no adhesion with the autologous graft. As a result of this construction, the user can use shaft knob 425 to selectively project measuring template 420 out of the distal end of hollow tube 405 or withdraw measuring template 420 back within the distal end of the hollow tube. Preferably, measuring template 420 has a tapered configuration adjacent to its proximal end (FIG. 24), and preferably the entrance to the distal end of hollow tube 405 has a tapered configuration (not shown in the drawings), such that retraction of the measuring template into the hollow tube causes the measuring template to automatically self-fold into a tubular configuration as the measuring template is withdrawn into the hollow tube. It will be appreciated that where the distal end of outer tube 405 is transparent, the folded measuring template 420 will be visible to the user when the measuring template has been withdrawn into outer tube 105. See FIGS. 27 and 28.

In use, the distal end of measuring template 420 is first withdrawn into hollow tube 405, and then the distal end of arthroscopic applicator tool and measuring template 400 is arthroscopically advanced to an implant site. Next, measuring template 420 is advanced out of the distal end of the tool and used (e.g., under endoscopic visualization) to measure the size of the defect which is to be restored with the autologous graft. These measurements may be recorded by hand, or by camera, or by arthroscopically marking the measuring template in situ (e.g., with a marking pen). Then measuring template 420 is withdrawn back into the interior of hollow tube 405, and the tool is withdrawn from the patient.

Next, the measuring template 420 is reduced in size to match the recorded size of the cartilage defect. This may be done on a "back table" by projecting measuring template 420 out of the distal end of hollow tube 405 and then cutting the measuring template down to size, e.g., with scissors. If desired, measuring template 420 may be returned to the site of the defect to confirm fit. With the sizing of measuring template 420 confirmed, measuring template 420 may then be used to size the autologous graft for proper seating at the implant site. By way of example but not limitation, this may be done by placing the autologous graft on the sized measuring template and then trimming off any graft overhang.

Once the autologous graft has been properly sized, the autologous graft is positioned on measuring template 420 (if it is not already on measuring template 420), and then the measuring template is withdrawn into the interior of hollow tube 405. This action causes the autologous graft, which is seated on the measuring template, to be folded along with the measuring template and carried into the hollow tube along with the measuring template. It will be appreciated that where the distal end of outer tube 405 is transparent, and where measuring template 420 is transparent, the autologous graft will be visible to the user when the autologous graft has been withdrawn into outer tube 405. Then the distal end of the tool is arthroscopically advanced to the implant site. Next, the measuring template (carrying the autologous graft with it) is advanced out the distal end of the tool and positioned adjacent to the implant site. Then the autologous graft is slid off the measuring template and onto the implant site, whereupon the autologous graft will either naturally adhere to the bone bed due to the natural adhesion between the bone bed and the autologous graft and/or an adhesive or a mechanical device (e.g., a dart) may be used to secure the autologous graft to the bone. Measuring template 420 is then withdrawn back into the interior of hollow tube 405, and finally the tool is withdrawn from the implant site.

In connection with the foregoing, it will be appreciated that arthroscopic applicator tool and measuring template 400 is intended to fold the autologous graft into the interior of the tool for transport to an interior surgical site. To this end, some autologous grafts may be more flexible than others. Therefore, with less flexible autologous grafts, the graft may be formed thinner so as to retain as much flexibility as possible—in this case, a graft of greater height may be formed in situ by sequentially delivering two or more individual grafts, with the individual grafts stacking one on top of another at the surgical site so as to form a final graft of the desired thickness. If desired, cement may be applied between successive layers of the graft to hold the layers in position relative to one another, and relative to the host bone.

Arthroscopic applicator tool and measuring template 400 may be used to measure the size of the cartilage defect while the joint is being irrigated with fluid (e.g., saline), or it may be used to measure the size of the defect in the absence of irrigation.

Arthroscopic applicator tool and measuring template 400 is preferably used to deliver the autologous graft to the implant site after irrigation has ceased.

3. Exemplary Procedure

FIGS. 32-44 show selected steps from an exemplary procedure for harvesting a tissue biopsy from a non-critical section of a joint, and sizing and seating an autologous graft at the implant site, using the novel instrumentation of the present invention.

Figure 32:
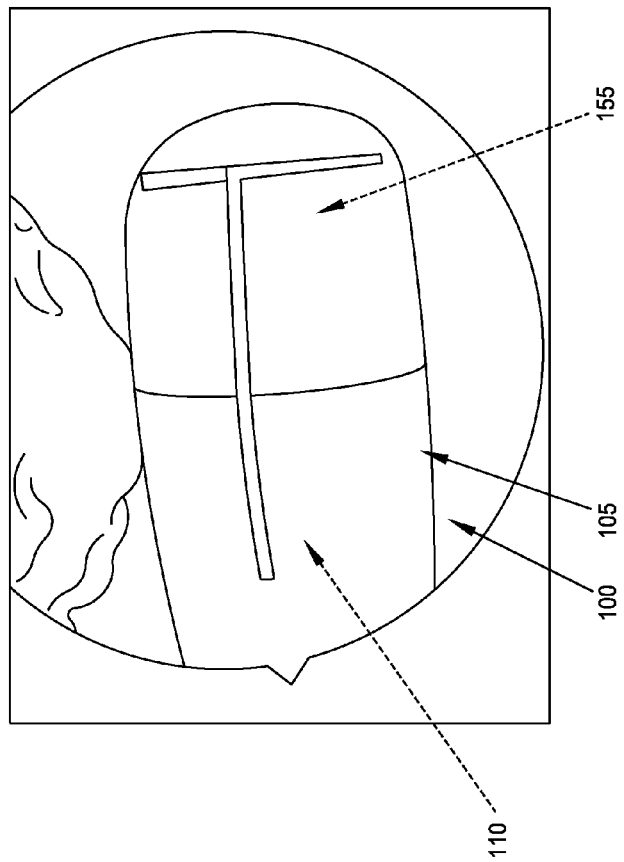
Figure 34:
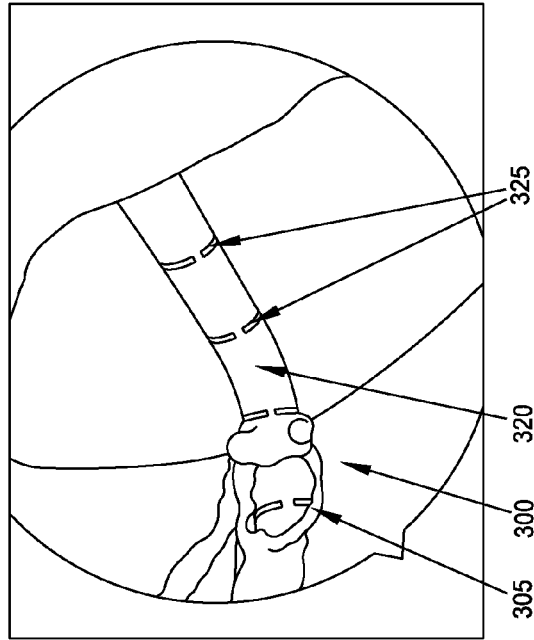
Figure 33:
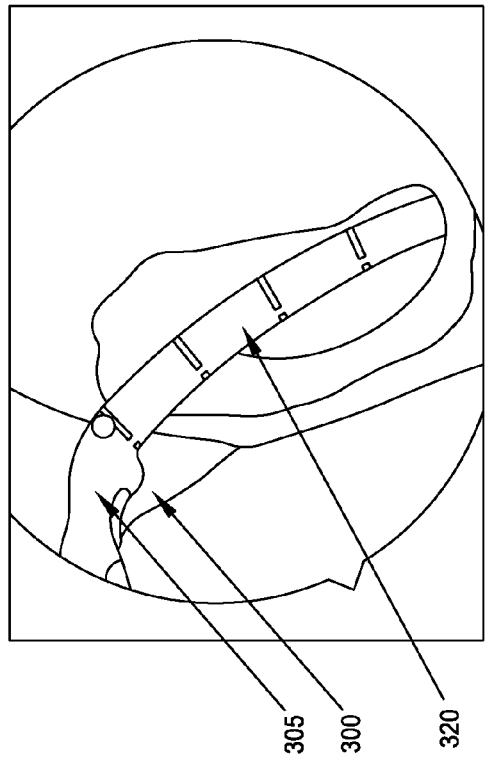
Figure 38:
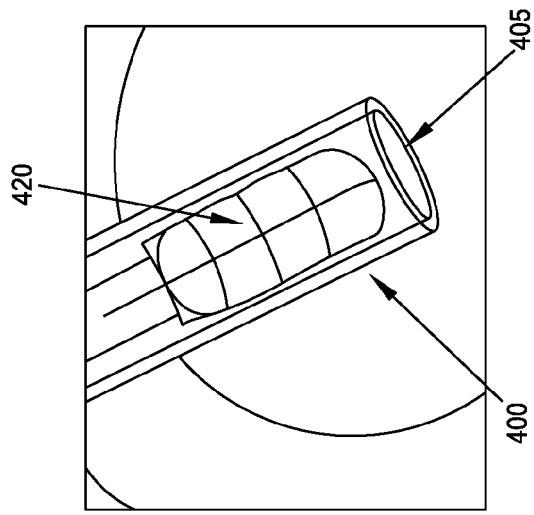
Figure 37:
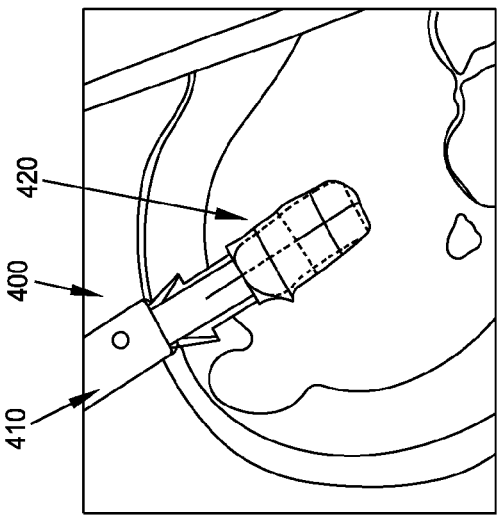
Figure 36:
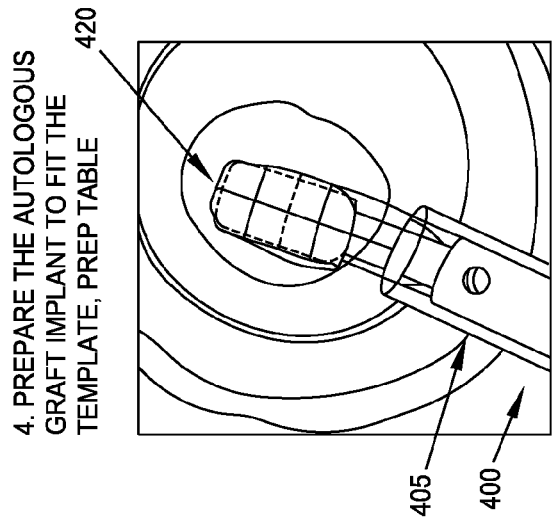
Figures 43, 44:
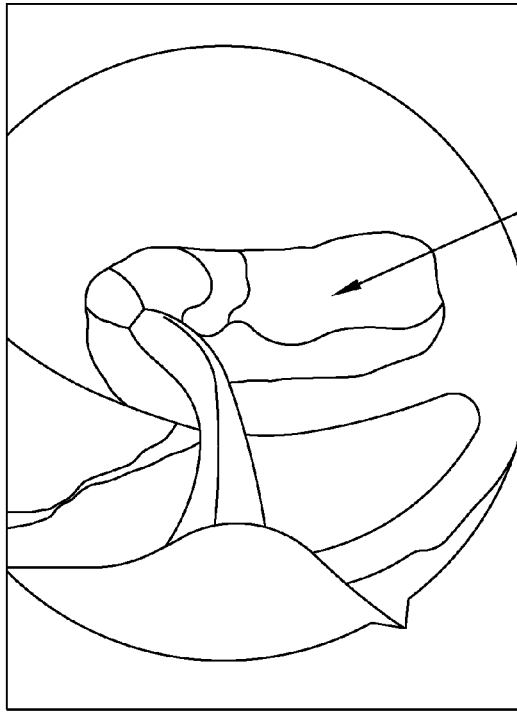

More particularly, FIG. 32 shows a tissue biopsy being taken from a non-critical section of a joint using the multi-blade cartilage biopsy tool 100. FIGS. 33 and 34 show arthroscopic tape measurer tool 300 measuring a defect site. FIG. 35 shows arthroscopic applicator tool and measuring template 400 having its measuring template 420 cut to size and the sized measuring template having its dimensions confirmed arthroscopically. FIGS. 36-38 show the autologous graft being sized to fit the sized measuring template 420 and being stored inside outer tube 405 of the arthroscopic applicator tool and measuring template 400. FIGS. 39-42 show arthroscopic applicator tool and measuring template 400 delivering the autologous graft to the implant site. And FIGS. 43 and 44 show the autologous graft having its position confirmed at the implant site.

MODIFICATIONS

It should also be understood that many additional changes in the details, materials, steps and arrangements of parts, which have been herein described and illustrated in order to explain the nature of the present invention, may be made by those skilled in the art while still remaining within the principles and scope of the invention.

What is claimed is:

1. A method for arthroscopically measuring objects and for applying an autologous graft to the anatomy of a patient, the method comprising:
   providing an arthroscopic measuring and applicator tool comprising:
      a tube having a distal end, a proximal end, and a lumen extending between the distal end and the proximal end; and
      a measuring and applicator element comprising a shaft having a distal end, a proximal end, and a longitudinal axis extending therebetween, and a measuring template mounted to the distal end of the shaft;
      the shaft of the measuring and applicator element being movably received within the lumen of the tube such that the distal end of the measuring template can project out the distal end of the tube or be withdrawn into the lumen of the tube; and
      the measuring template comprising a distal end and a proximal end and a longitudinal axis extending therebetween, the longitudinal axis of the measuring template being parallel to the longitudinal axis of the shaft, and the measuring template being foldable along its longitudinal axis so that the measuring template is transformable between a planar configuration and a tubular configuration;
   positioning the measuring template within the tube, with the measuring template being in its tubular configuration;
   advancing the distal end of the tube to an interior site;
   advancing the measuring template out of the tube so that the measuring template transforms into its planar configuration;
   using the measuring template to measure an object at an interior site;
   retracting the measuring template into the tube so that the measuring template transforms into its tubular configuration;
   withdrawing the distal end of the tube from the interior site;
   advancing the measuring template out of the tube so that the measuring template transforms into its planar configuration, and positioning the measuring template adjacent to an autologous graft;
   using the measuring template to size an autologous graft;
   positioning the sized autologous graft on the measuring template;
   retracting the measuring template and the autologous graft into the tube so that the measuring template transforms into its tubular configuration;
   advancing the distal end of the tube to a graft site;
   advancing the measuring template out of the tube so that the measuring template transforms into its planar configuration; and
   positioning the autologous graft at the graft site.

2. A method according to claim 1 wherein the measuring template has a tapered configuration adjacent to its proximal end so that retraction of the measuring template into the tube causes the measuring template to automatically self-fold into its tubular configuration as the measuring template is withdrawn into the tube.

3. A method according to claim 1 wherein the measuring template is formed out of a material which provides minimal adhesion with an autologous graft.

4. A method according to claim 1 wherein the measuring template is transparent.

5. A method according to claim 1 wherein the measuring template comprises measurement markings.

6. A method according to claim 1 wherein the measuring template is formed out of material which is cuttable.

7. A method according to claim 1 wherein at least the distal end of the tube is transparent.

* * * * *